US012678411B2

(12) United States Patent
Sampen et al.

(10) Patent No.: US 12,678,411 B2
(45) Date of Patent: Jul. 14, 2026

(54) NANOFORMULATIONS OF PAZOPANIB, COMPOSITIONS COMPRISING THE SAME AND METHODS OF TREATING OSTEOARTHRITIS

(71) Applicants: The United States Government as represented by the Department of Veterans Affairs, Washington, DC (US); The Board of Trustees of the University of Illinois, Urbana, IL (US)

(72) Inventors: Hee-Jeong Im Sampen, Chicago, IL (US); Ying Liu, Chicago, IL (US)

(73) Assignees: THE UNITED STATES GOVERNMENT AS REPRESENTED BY THE DEPARTMENT OF VETERANS AFFAIRS, Washington, DC (US); The Board of Trustees of the University of Illinois, Urbana, IL (US)

( * ) Notice: Subject to any disclaimer, the term of this patent is extended or adjusted under 35 U.S.C. 154(b) by 265 days.

(21) Appl. No.: 18/568,019

(22) PCT Filed: Jun. 8, 2022

(86) PCT No.: PCT/US2022/032663
§ 371 (c)(1),
(2) Date: Dec. 7, 2023

(87) PCT Pub. No.: WO2022/261199
PCT Pub. Date: Dec. 15, 2022

(65) Prior Publication Data
US 2024/0180846 A1     Jun. 6, 2024

Related U.S. Application Data

(60) Provisional application No. 63/208,137, filed on Jun. 8, 2021.

(51) Int. Cl.
*A61K 9/51* (2006.01)
*A61K 9/00* (2006.01)
*A61K 31/506* (2006.01)
*A61K 35/28* (2015.01)
*A61K 47/26* (2006.01)
*A61P 19/02* (2006.01)

(52) U.S. Cl.
CPC .......... *A61K 9/5153* (2013.01); *A61K 9/0019* (2013.01); *A61K 31/506* (2013.01); *A61K 35/28* (2013.01); *A61K 47/26* (2013.01); *A61P 19/02* (2018.01)

(58) Field of Classification Search
CPC .. A61K 9/5153; A61K 9/0019; A61K 31/506; A61K 35/28; A61K 47/26; A61K 9/5146; A61P 19/02; A61P 19/00; A61P 21/00
See application file for complete search history.

(56) References Cited

U.S. PATENT DOCUMENTS

2018/0243294 A1     8/2018  Nguyen et al.

FOREIGN PATENT DOCUMENTS

WO     WO-2019/220441 A1     11/2019

OTHER PUBLICATIONS

Brambilla R, et al. "Inhibition of astroglial nuclear factor kappaB reduces inflammation and improves functional recovery after spinal cord injury." JEM 2005, 202(1):145-156.
Clark-Raymond A, and Halaris A. "VEGF and depression: a comprehensive assessment of clinical data." J Psychiatric Research, 2013 47:1080.
Das V, et al. "Blockade of Vascular Endothelial Growth Factor Receptor-1 (Flt-1), Reveals a Novel Analgesic For Osteoarthritis-Induced Joint Pain." Gene Reports 2018, 11:94-100.
Dominick KL, et al. "Arthritis prevalence and symptoms among US non-veterans, veterans, and veterans receiving Department of Veterans Affairs Healthcare." J Rheumatol. 2006;33(2):348-354.
Fnu et al. (2019) "Pazopanib Loaded PLGA Nanoparticles for the Treatment of Age-related Macular Degeneration," University of South Florida, pp. 1-28.
Im HJ, et al. (2010). "Alteration of sensory neurons and spinal response to an experimental osteoarthritis pain model." Arthritis Rheum 62:2995-3005.
Ji TJ, et al. "An Avascular Niche Created by Axitinib-Loaded PCL/Collagen Nanofibrous Membrane Stabilized Subcutaneous Chondrogenesis of Mesenchymal Stromal Cells," Advance Science 2021, 2100351.
Kc R, et al. "PKCo null mutations in a mouse model of osteoarthritis alter osteoarthritic pain independently of joint pathology by augmenting NGF/TrkA-induced axonal outgrowth." Ann Rheum Disease 2016 75(12):2133.
Knights CB, et al. "Partial medial meniscectomy produces osteoarthritis pain-related behaviour in female C57BL/6 mice." Pain. Feb. 2012;153 (2):281-92.

(Continued)

*Primary Examiner* — Quanglong N Truong
(74) *Attorney, Agent, or Firm* — BALLARD SPAHR LLP

(57)     ABSTRACT

Disclosed herein are nanoparticles comprising Pazopanib or a derivative thereof encapsulated by the copolymer poly (lactic-co-glycolic acid) (PLGA). Also disclosed herein are methods for treating osteoarthritis, inhibiting or preventing cartilage degeneration, and reducing or inhibiting pain-associated depression in subjects with joint pain with nanoparticles comprising Pazopanib or a derivative thereof.

19 Claims, 20 Drawing Sheets

(56) References Cited

OTHER PUBLICATIONS

Kotlarz H, et al. "Insurer and out-of-pocket costs of osteoarthritis in the US: evidence from national survey data." Arthritis Rheum. 2009 60, 3546-3553.

Kroin JS, et al. "Intraarticular slow-release triamcinolone acetate reduces allodynia in an experimental mouse knee osteoarthritis model." Gene. 2016. 10; 591(1): 1-5.

Liu, Y., et al. (2008) "Mixing in a multi-inlet vortex mixer (MIVM) for flash nano-precipitation." Chemical Engineering Science, 63(11), 2829-2842.

Mcclendon J, et al., "Cumulative Disadvantage and Disparities in Depression and Pain Among Veterans With Osteoarthritis: The Role of Perceived Discrimination." Arthritis Care & Research 2021 73:11-17.

Nowacka-Chmielewska MM, et al. "Alterations in VEGF expression induced by antidepressant drugs in female rats under chronic social stress." Experimental and Therapeutic Medicine 2017, 13:723-730.

Richardson LM, et al., "Patient prioritization of comorbid chronic conditions in the Veteran population: Implications for patient-centered care." SAGE Open Medicine, 2016. 4:1-11.

Roughan WH, et al., "Comorbid Chronic Pain and Depression: Shared Risk Factors and Differential Antidepressant Effectiveness." Frontiers in Psychiatry, 2021, 12:1.

Schrodt MV and Ankrum JA. "Chemomechanically antifibrotic stromal cells." Nature Biomedical Engineering 2022, 6:6-7.

Shen, H.; et al. (2011) "Self-assembling process of flash nanoprecipitation in a multi-inlet vortex mixer to produce drug-loaded polymeric nanoparticles." Journal of Nanoparticle Research, pp. 1-28.

Satue et al. "Intra-articularly injected mesenchymal stem cells promote cartilage regeneration, but do not permanently engraft in distant organs." Scientific Rep. 2019, 9:10153.

Stanishewski M and Zimmermann B. "Osteoarthritis Treatment in the Veteran Population." Fed Pract. 2015. 32(Supp 12): 21S-25S.

Sun et al., "Allogeneic Mesenchymal Stem Cells as Induction Therapy are Safe and Feasible in Renal Allografts: pilot results of a multicenter Randomized Controlled Trial," J. Transl. Med. 16:52 1-10, (2018).

Szymusiak, M., et al. (2016). "Bioavailability of curcumin and curcumin glucuronide in the central nervous system of mice after oral delivery of nano-curcumin." Int J Pharm. 511(1), 415-423.

Thompson WL, et al. "Inflammatory cytokines stimulate the chemokines CCL2/MCP-1 and CCL7/MCP-3 through NFkB and MAPK dependent pathways in rat astrocytes [corrected]." Brain Res. Sep. 1, 2009;1287:47-57.

Vasquez, KO and Peterson, JD. "Early Detection of Acute Drug-Induced Liver Injury in Mice by Noninvasive Near-Infrared Fluorescence Imaging." J Pharmacol Exp Ther 2017, 361:87-98.

Wong SW, et al. "Controlled Deposition of 3D Matrices to Direct Single Cell Functions." Advanced Science 2020 7, 2001066.

Wong SW, et al. "Inhibition of aberrant tissue remodelling by mesenchymal stromal cells singly coated with soft gels presenting defined chemomechanical cues." Nature Biomedical engineering 2022, 6:54-66.

Zheng S. et al., "Depression in patients with knee osteoarthritis: risk factors and associations with joint symptoms." BMC Musculoskeletal Disorders 2021 22:40.

International Search Report and Written Opinion were mailed on Aug. 30, 2022 by the International Searching Authority for International Application No. PCT/US2022/032663, filed on Jun. 8, 2021 and published as WO/2022/261199 on Dec. 15, 2022 (Applicant—The United States Government as Represented by the Department of Veterans Affairs) (8 Pages).

Dang, Y., et al., "Stem cell therapies for age-related macular degeneration: the past, present, and the future," Clinical Interventions in Aging, p. 255 (2015).

Krishnamurthy, S., et al., "Lipid-coated polymeric nanoparticles for cancer drug delivery," Biomaterials Science, 3(7): 923-936 (2015).

Nago,M., et al., "Vascular Endothelial Growth Factor in Cartilage Development and Osteoarthritis," Scientific Reports, 7(1) (2017).

Pers,Y-M, et al., "Mesenchymal stem cells for the management of inflammation in osteoarthritis: state of the art and perspectives," Osteoarthritis and Cartilage, Elsevier, 23(11): 2027-2035 (2015.

Sham + Vehicle                 PMM + Vehicle                 PMM + Nano-PAZIII

A.　Sucrose preference test (SPT)

B.　Open field test (OFT)

NANOFORMULATIONS OF PAZOPANIB, COMPOSITIONS COMPRISING THE SAME AND METHODS OF TREATING OSTEOARTHRITIS

CROSS REFERENCE TO RELATED APPLICATIONS

This application is a national phase filing under 35 U.S.C. § 371 of International Application No. PCT/US2022/032663, filed Jun. 8, 2022, which claims the benefit of U.S. Provisional Application No. 63/208,137, filed Jun. 8, 2021. The content of these earlier filed applications is hereby incorporated by reference herein in their entirety.

BACKGROUND

Osteoarthritis (OA) is the most common form of arthritis. It is a leading cause of debilitating pain and disability, affecting more than 32 million in the U.S. Worse, the prevalence and incidence of OA have been increasing due to increases in lifespan and obesity and are expected to rise to more than 78 million in the U.S. by 2040. The association of an elevated OA incidence with the military population is particularly significant as a leading cause of disability among the military population.

The annual economic burden of $185 billion caused by OA disease is alarming. Unfortunately, clinically accepted treatment strategies do not cure OA, are often ineffective, and there is over-reliance on opioids for pain. Recent insurance claim data indicate that over 50% of OA patients have been treated with opioids, and many have become opioid-dependent. These high rates of chronic pain and subsequent opioid over-treatment have become a significant health concern in this society among military and civilian populations in the U.S. Many cases eventually require joint replacement with a prosthesis, which is costly, and the limited functional life of prostheses (~10 y) can make a second replacement necessary. These factors increase the overall cost of treatment and the risk for associated morbidity. Importantly, surgical procedures to address OA typically do not result in a pain-free cure. Despite the major negative impact of chronic pain on quality of life and health care management, there is no way as yet to cure or prevent its progression. Also, there is no OA-specific anti-pain medication. Thus, there is an urgent, unmet need to identify OA targets and develop OA disease-modifying drugs to control chronic joint pain and halt OA pathological progression.

SUMMARY

Disclosed herein are nanoparticles comprising or consisting of Pazopanib or a derivative thereof encapsulated by the copolymer poly(lactic-co-glycolic acid) (PLGA).

Disclosed herein are compositions comprising two or more nanoparticles comprising or consisting of Pazopanib or a derivative thereof encapsulated by the copolymer poly(lactic-co-glycolic acid) (PLGA).

Disclosed herein are pharmaceutical compositions comprising one or more nanoparticles comprising or consisting of Pazopanib or a derivative thereof encapsulated by the copolymer poly(lactic-co-glycolic acid) (PLGA).

Disclosed herein are methods of inhibiting cartilage degeneration in a subject, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of reducing pain or reducing joint pain in a subject, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of protecting cartilage or preventing cartilage degeneration in a subject, the methods comprising administering to a subject in need thereof a therapeutically effective amount of a composition comprising a nanoparticle comprising or consisting of Pazopanib or a derivative thereof encapsulated by the copolymer poly (lactic-co-glycolic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of preventing or reducing or inhibiting pain-associated depression in a subject, the methods comprising administering to a subject in need thereof a therapeutically effective amount of a composition comprising a nanoparticle comprising or consisting of Pazopanib or a derivative thereof encapsulated by the copolymer poly (lactic-co-glycolic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of reducing spinal activation of NF-kB glial axis in a subject, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of treating osteoarthritis in a subject in need thereof, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly (lactic-co-glycolic acid) (PLGA).

Disclosed herein are methods of reducing or ameliorating one or more symptoms of osteoarthritis in a subject, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly(lactic-co-gly-colic acid) (PLGA).

Disclosed herein are methods of treating a joint disease in a subject in need thereof, the methods comprising administering to a subject in need thereof a therapeutically effective amount of a composition comprising a nanoparticle comprising or consisting of Pazopanib or a derivative thereof encapsulated by the copolymer poly(lactic-co-glycolic acid) (PLGA) or a pharmaceutical composition comprising one or more nanoparticles comprising or consisting of Pazopanib or a derivative thereof encapsulated by the copolymer poly (lactic-co-glycolic acid) (PLGA).

Disclosed herein are methods of treating a joint condition in a subject in need thereof, the methods comprising administering to a subject in need thereof a therapeutically effective amount of a composition comprising a nanoparticle comprising or consisting of Pazopanib or a derivative thereof encapsulated by the copolymer poly(lactic-co-gly-colic acid) (PLGA) or a pharmaceutical composition comprising one or more nanoparticles comprising or consisting of Pazopanib or a derivative thereof encapsulated by the copolymer poly(lactic-co-glycolic acid) (PLGA).

Disclosed herein are methods of enhancing tissue regeneration in a subject in need thereof, the methods comprising administering to a subject in need thereof a therapeutically effective amount of a composition comprising a nanoparticle comprising or consisting of Pazopanib or a derivative thereof encapsulated by the copolymer poly(lactic-co-gly-colic acid) (PLGA) or a pharmaceutical composition comprising one or more nanoparticles comprising or consisting of Pazopanib or a derivative thereof encapsulated by the copolymer poly(lactic-co-glycolic acid) (PLGA) and mesenchymal stem cells.

Figures 7A, 7B, 7C, 7D:
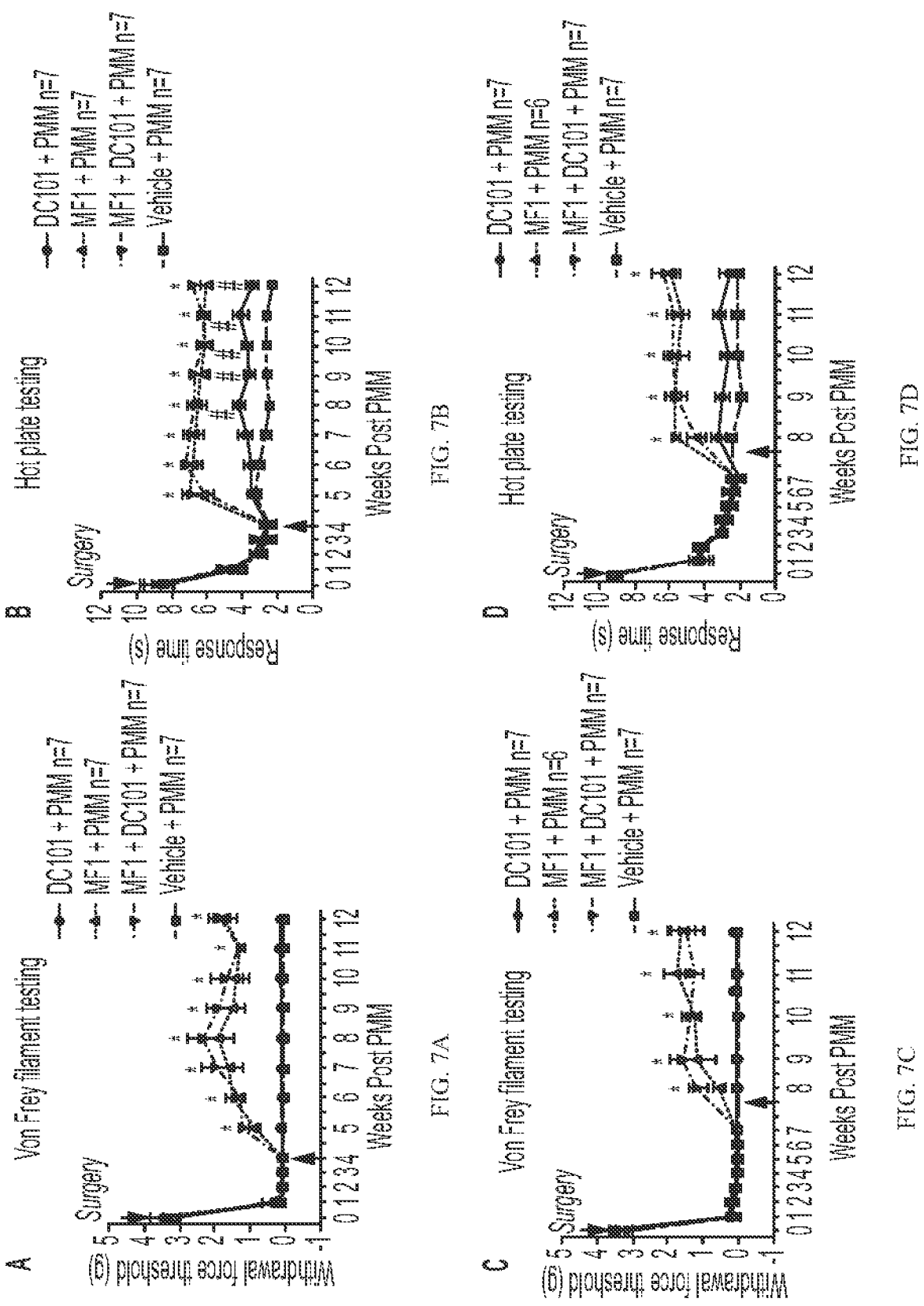

FIGS. 7A-D show mechanical allodynia (FIGS. 7A, 7C) or temperature sensitivity (FIGS. 7B, 7D) after weekly IA injections of 5 μg/knee mAb targeting VEGFR1 (by MF1) and/or VEGFR2 (by DC101) during early OA (4 weeks post-PMM, FIGS. 7A, 7B) or later OA stages (8 weeks post-PMM, FIGS. 7C, 7D). Rapid pain reduction shown after IA injection with MF1 but not by DC101. *p<0.05, compared to vechicle+PMM. PMM=partial medial meniscectomy.

Figure 8:
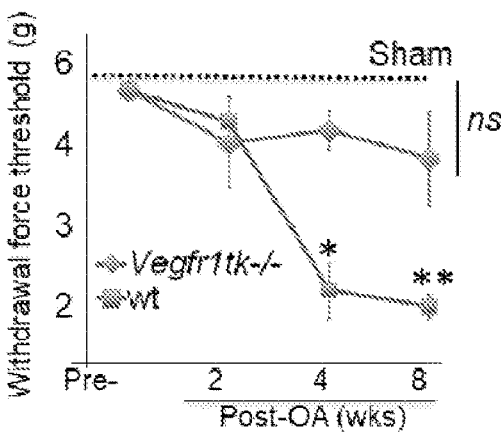

FIG. 8 shows mechanical allodynia in vegfr1tk$^{-/-}$ mice with knee joint OA compared to WT.

Figure 9A:
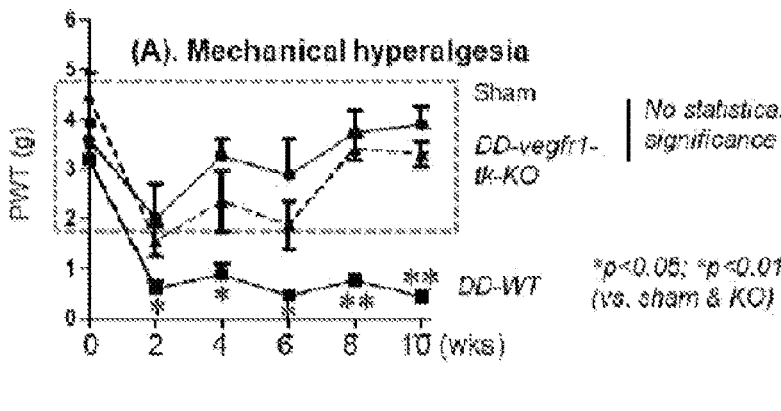
Figure 9B:
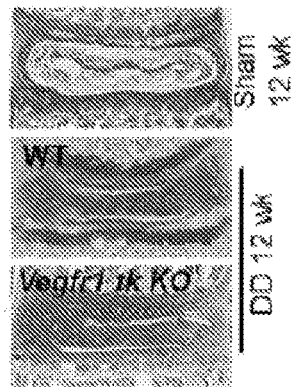

FIGS. 9A-B show reduced pain response (FIG. 9A) and histology of lumbar disc (FIG. 9B) in Vegfr1tk$^{-/-}$ mice compared to WT.

Figure 10:
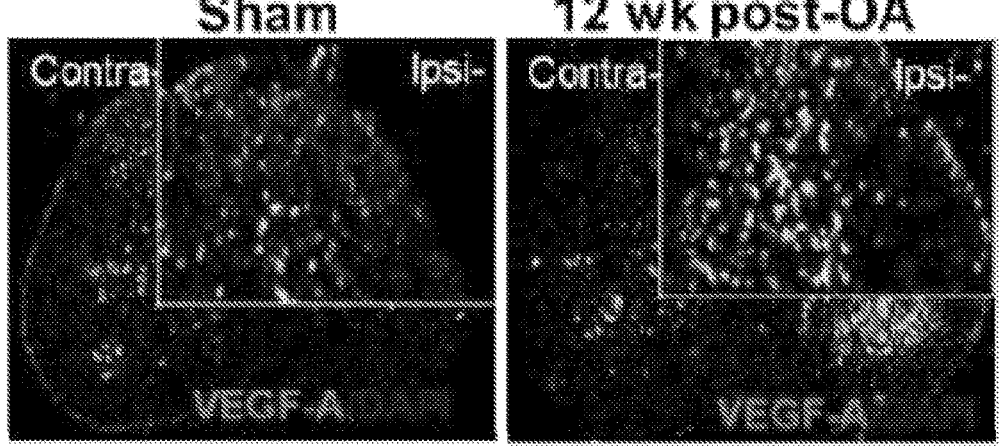

FIG. 10 shows an immunofluorescence comparison of VEGF-A in the spinal dorsal in sham and advanced osteoarthritis (OA).

Figure 11:
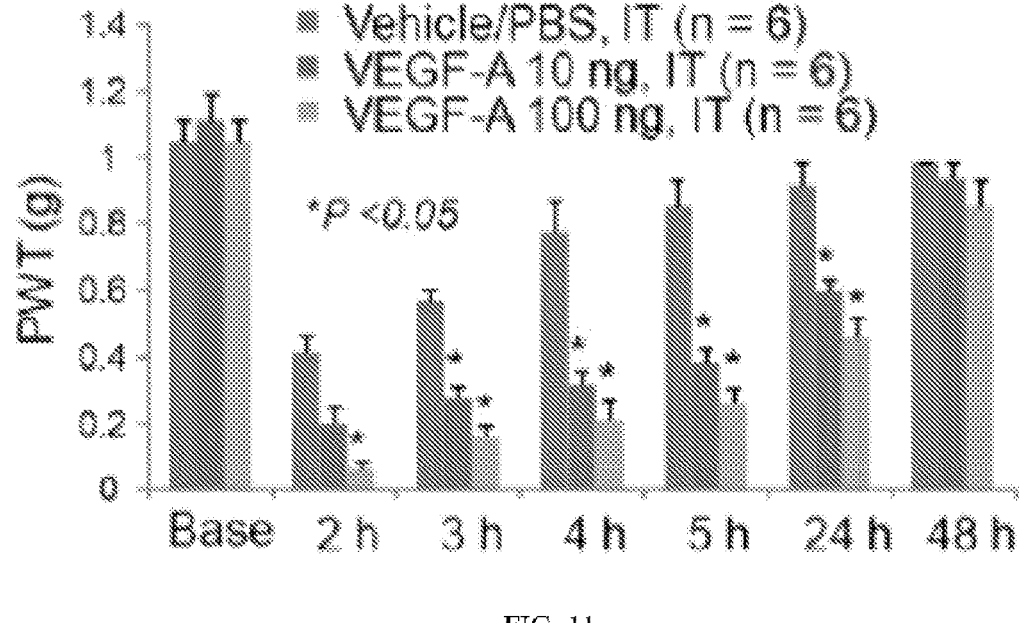

FIG. 11 shows mechanical hyperalgesia following intrathecal (IT) injection of VEGF-A (10 ng and 100 ng) in mice.

Figure 12:
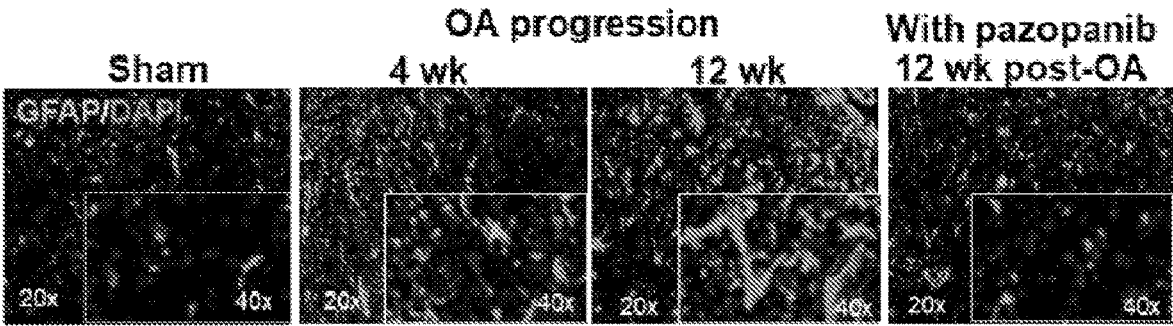

FIG. 12 shows the astroglial activity of spinal cord harvested from animals at 4 weeks and 12 weeks after osteoarthritis (OA) induction by -immunofluorescent targeting astroglial marker, GFAP.

Figure 13:
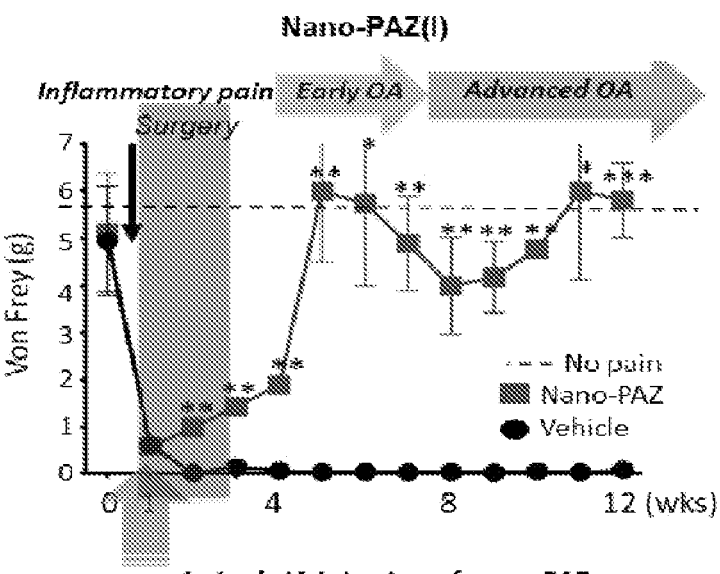

FIG. 13 shows that a single intraarticular (IA) injection of 32.5 μg nano-PAZ(I) (PEG-PCL) at surgery-induced inflammatory pain stage sustained the drug effect for >12 weeks. p<0.01, *p<0.001

Figure 14:
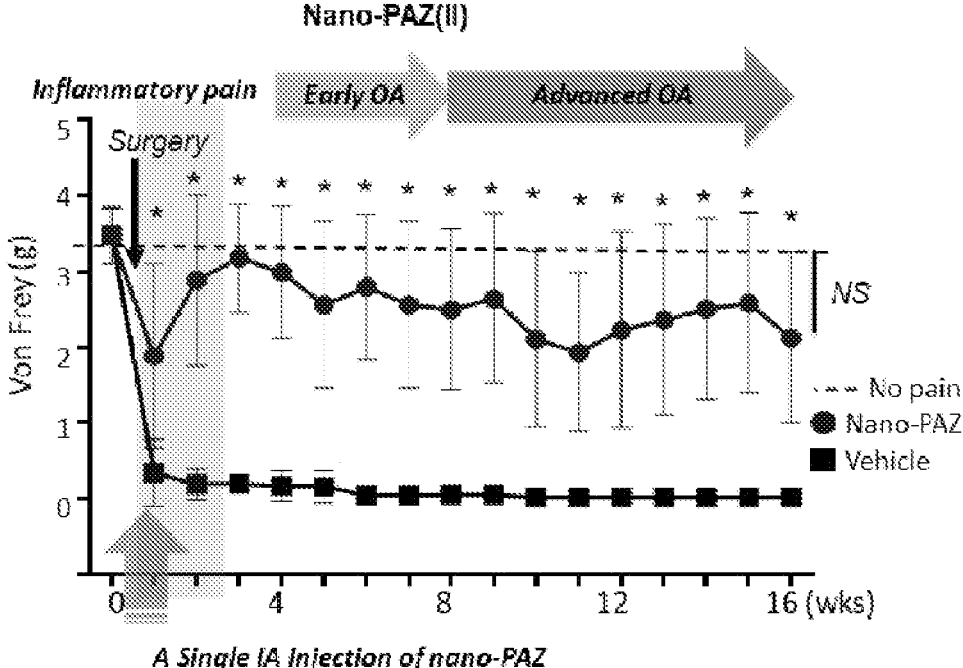

FIG. 14 shows that a single intraarticular (IA) injection of 32.5 μg nano-PAZ(II) (PEG-PLGA) at surgery-induced inflammatory pain stage sustained the drug effect for >16 weeks. *p<0.05 (Vehicle vs. Nano-PAZ); NS, no statistical significance.

Figure 15A:
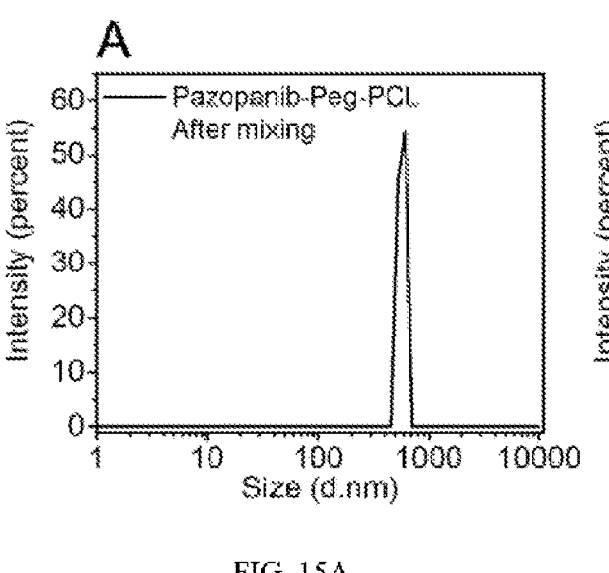
Figure 15B:
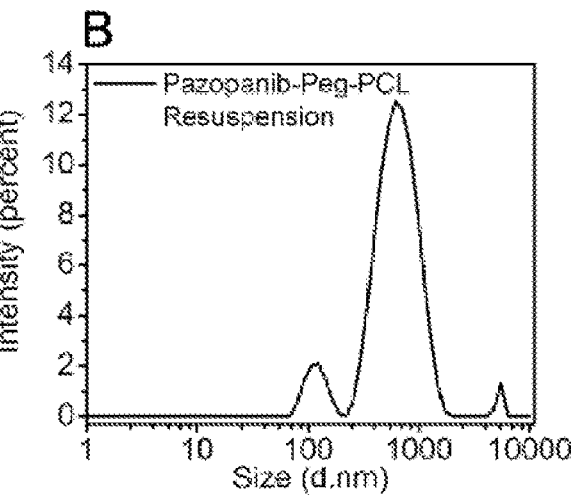

FIGS. 15A-B show the size distributions of the Paz-PEG-PCL nanosuspension right after flash nanoprecipitation (FIG. 15A) and after resuspension at 6 mg/ml (FIG. 15B) before intraarticular (IA) injection.

Figure 16A:
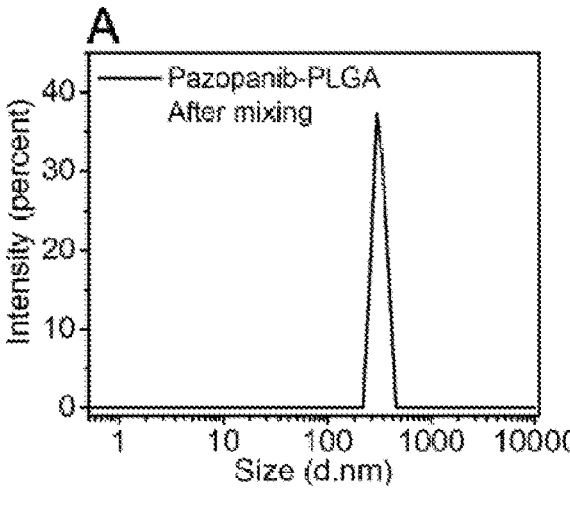
Figure 16B:
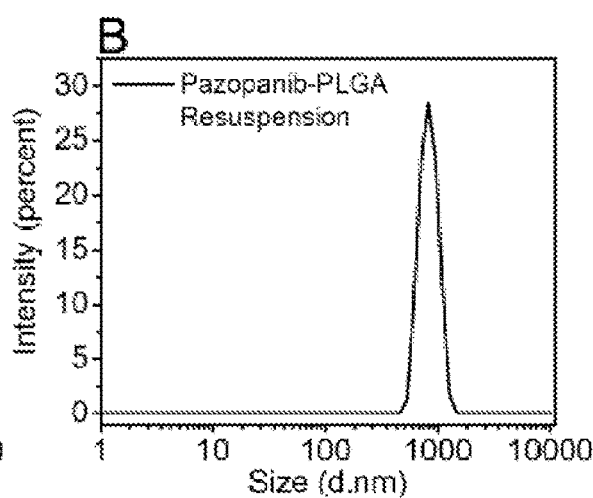

FIGS. 16A-B show the size distributions of the Paz-PLGA nanosuspension right after flash nanoprecipitation (FIG. 16A) and after resuspension at 6 mg/ml (FIG. 16B) before intraarticular (IA) injection.

Figure 17A:
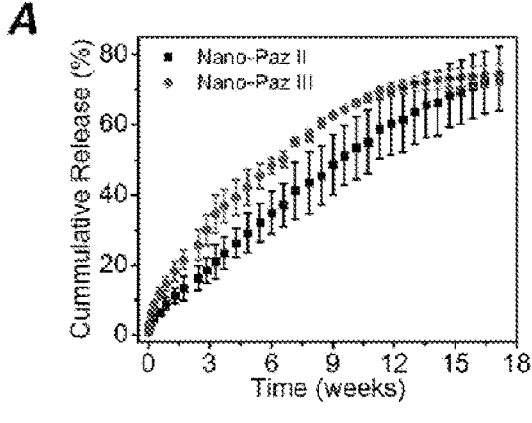
Figure 17A:
Figure 17B:
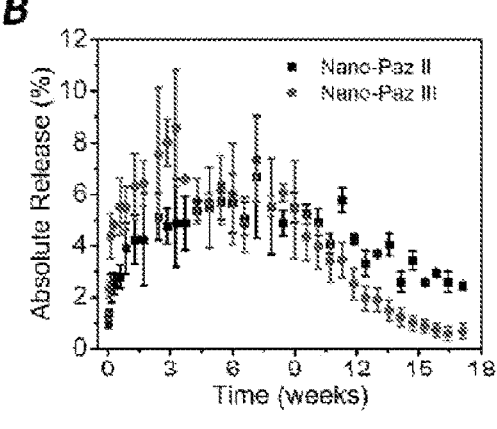

FIGS. 17A-B show in vitro release for Nano-Paz I (squares) and Nano-Paz II (circles). FIG. 17A shows the cumulative drug release. The amount was normalized by the initial total mass of the loaded drug. FIG. 17B shows the absolute drug release of each time point.

Figures 18A, 18B, 18C:
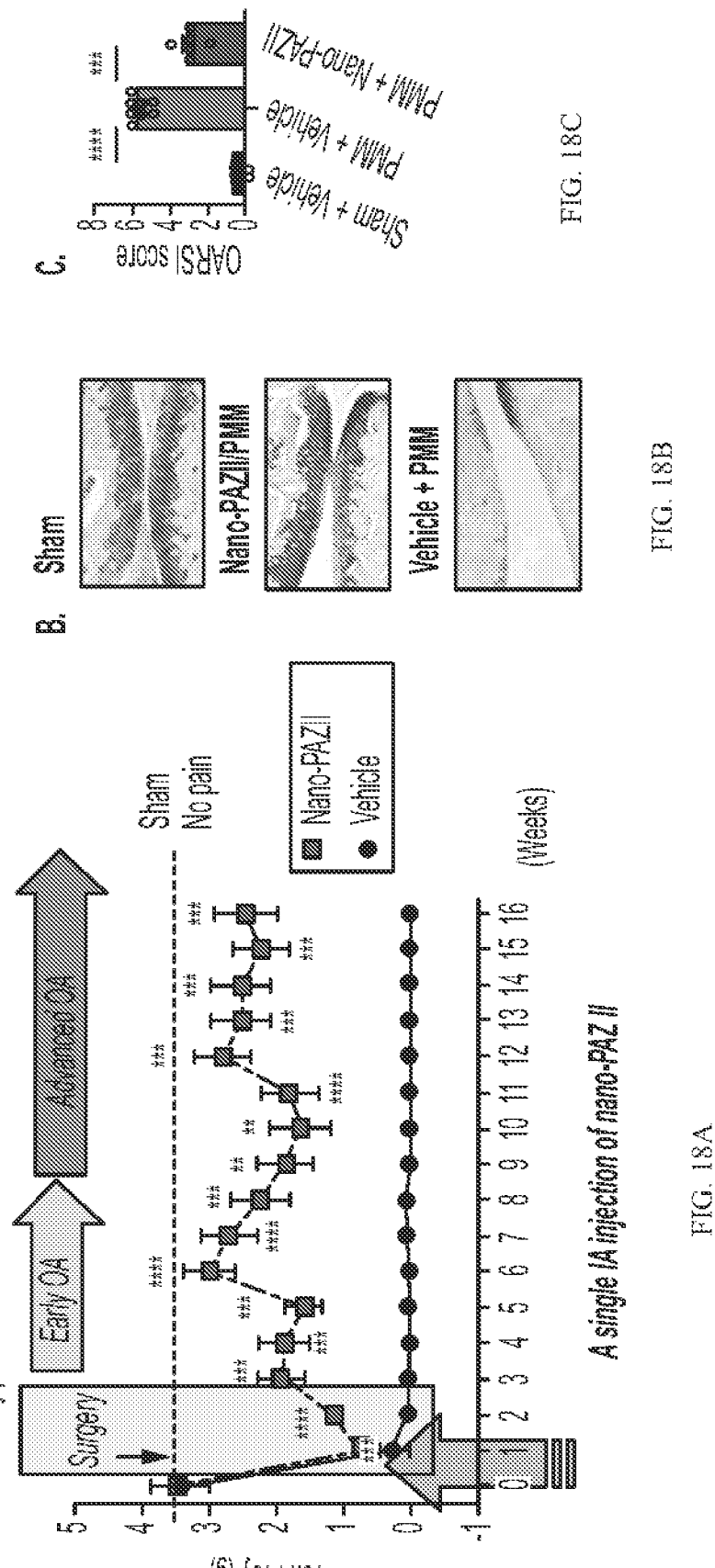

FIGS. 18A-C show the results of a single intraarticular (IA) injection of nano-PAZ II. FIG. 18A shows that a single IA injection of nano-PAZII at the time of joint injury sustains the drug effect for >16 weeks. p<0.01, *p<0.001, ****p<0.0001. FIG. 18B shows the histopathological analyses by safranin O-staining show excellent cartilage protection. FIG. 18C shows the quantitation of pathology by OARSI score.

Figures 19A, 19B, 19C:
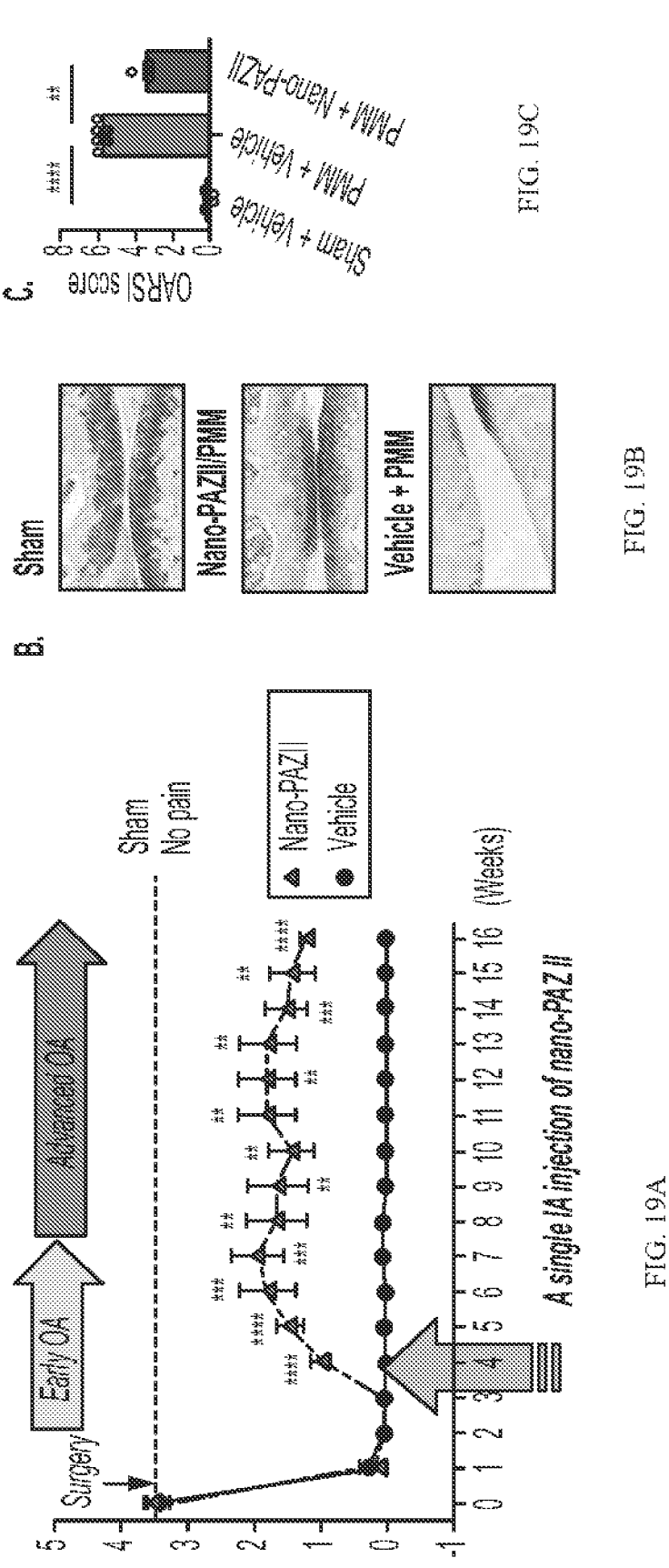

FIGS. 19A-C show the results of a single intraarticular (IA) injection of nano-PAZ II at the early OA stage. FIG. 19A shows that a single IA injection of nano-PAZII at early OA stage prolongs pain relief until 16 week post-PMM. p<0.01, *p<0.001, ****p<0.0001. FIG. 19B shows the histopathological analyses by safranin O-staining show partial protection of cartilage. FIG. 19C shows the quantitation of pathology by OARSI score. PMM=partial medial meniscectomy.

Figures 20A, 20B, 20C:
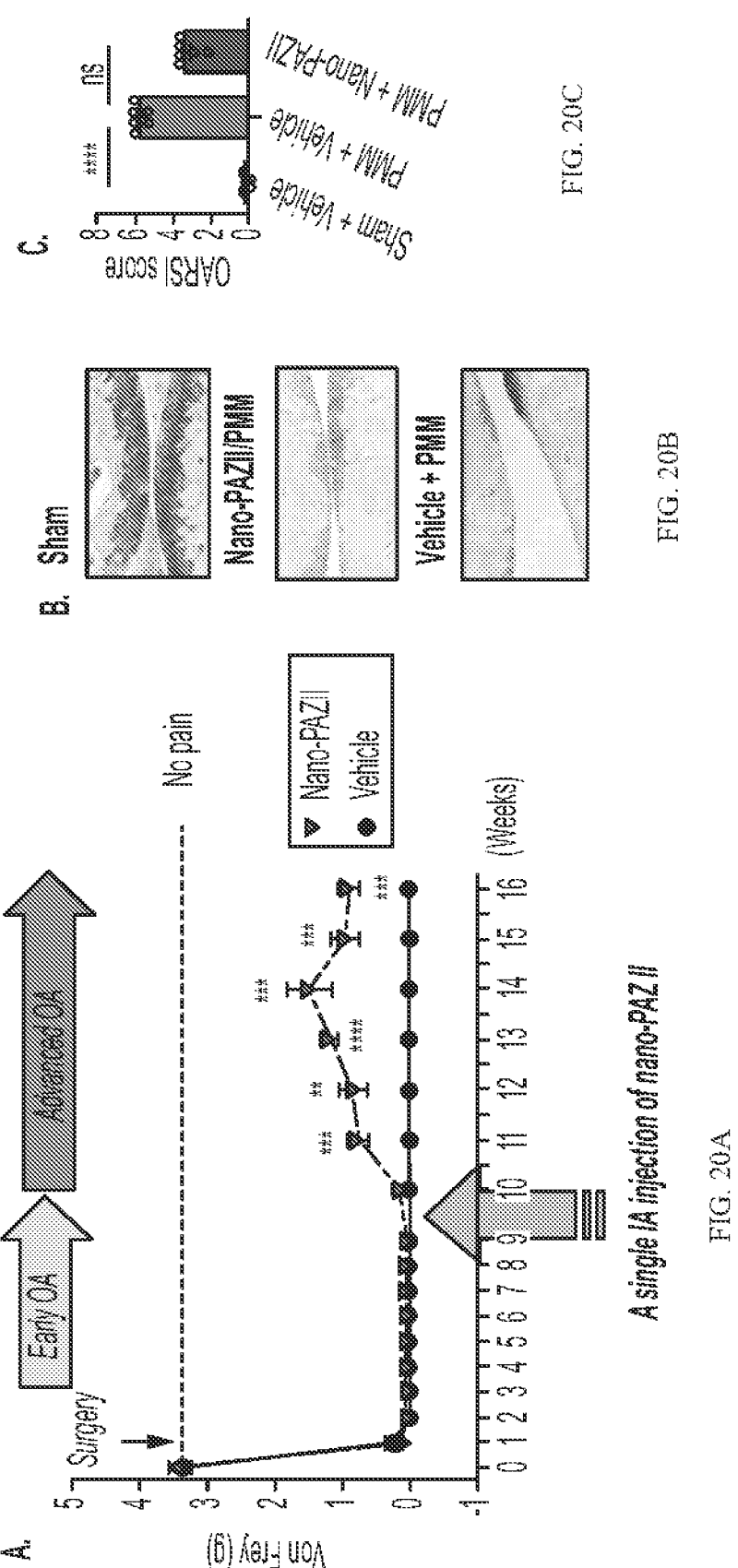

FIGS. 20A-C show the results of a single intraarticular (IA) injection of nano-PAZ II at advanced OA stage. FIG.

20A shows that a single IA injection of nano-PAZII at advanced OA stage prolongs pain relief until 16 week post-PMM. *p<0.05; p<0.01, *p<0.001, ****p<0.0001. FIG. 20B shows the histopathological analyses by safranin O-staining show partial protection of cartilage. FIG. 20C shows the quantitation of pathology by OARSI score. PMM=partial medial meniscectomy.

Figure 21:
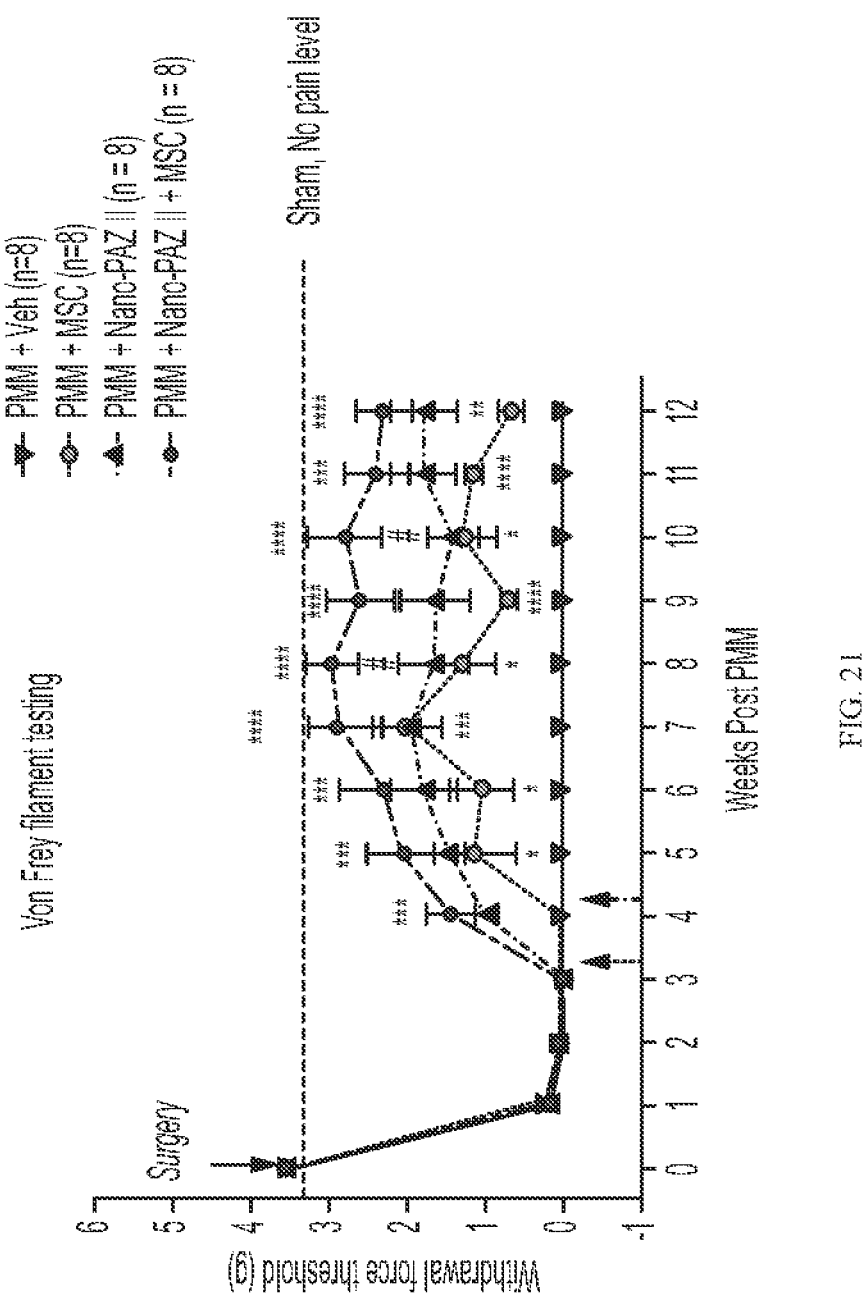

FIG. 21 shows that mechanical allodynia after a single intraarticular (IA) drug treatment targeting early OA stage. A single nano-PAZII injection is indicated by the first arrow and a single MSC injection is indicated by the second arrow. Pain reduction is markedly reduced with combined treatments of nano-PAZII and MSCs (circles) compared with nano-PAZI1 alone (triangles) #p<0.05.

Figures 22A, 22B:
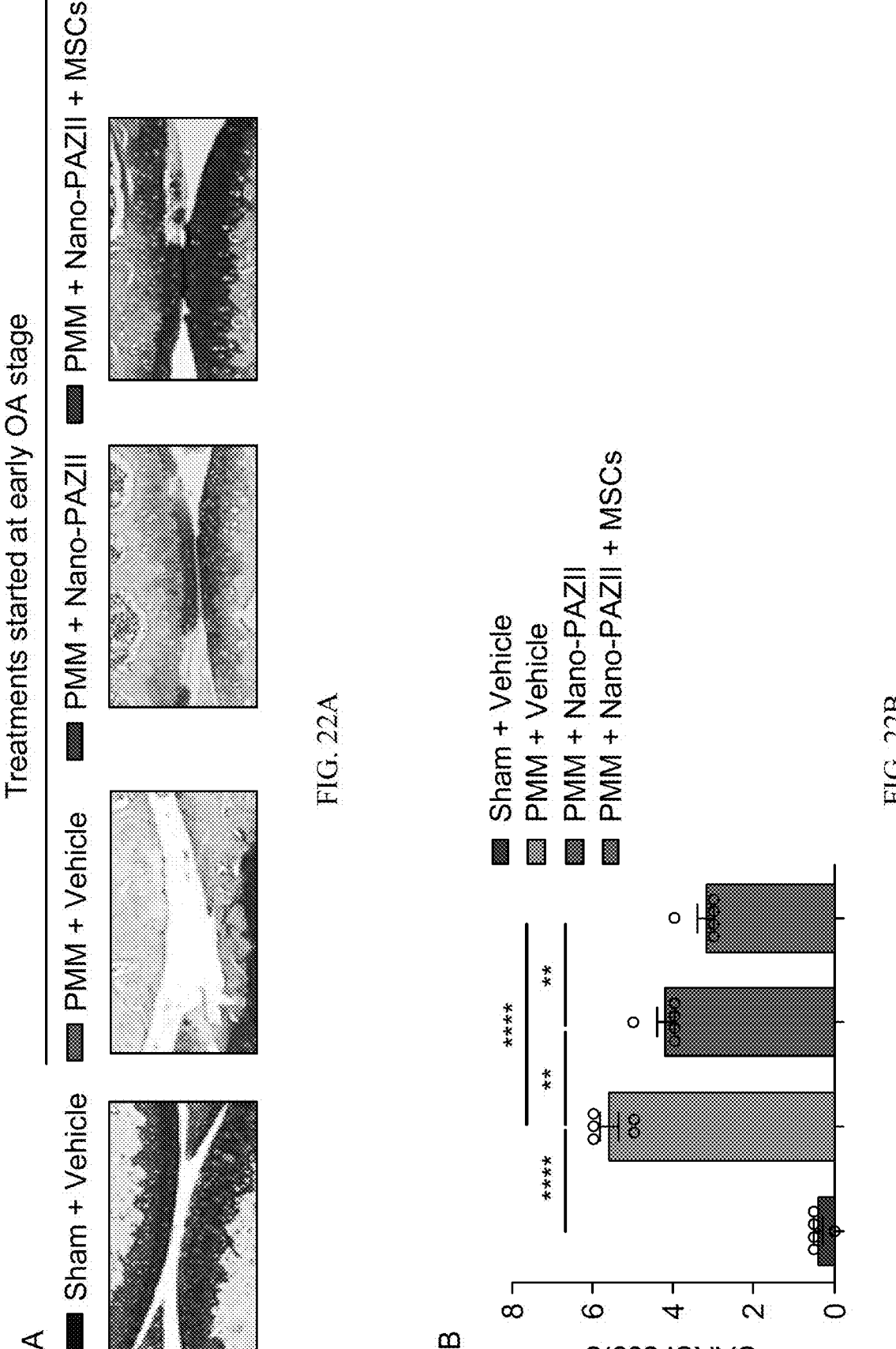

FIGS. 22A-B show that the effect of a single intraarticular (IA) injection of Nano-Paz II combined with MSCs on joint pathology. FIG. 22A show representative images of safranin-0 fast green staining of the knee joints. FIG. 22B shows the auantification of pathology by the OARSI scores (n=5). p<0.01, **p<0.0001).

Figure 23A:
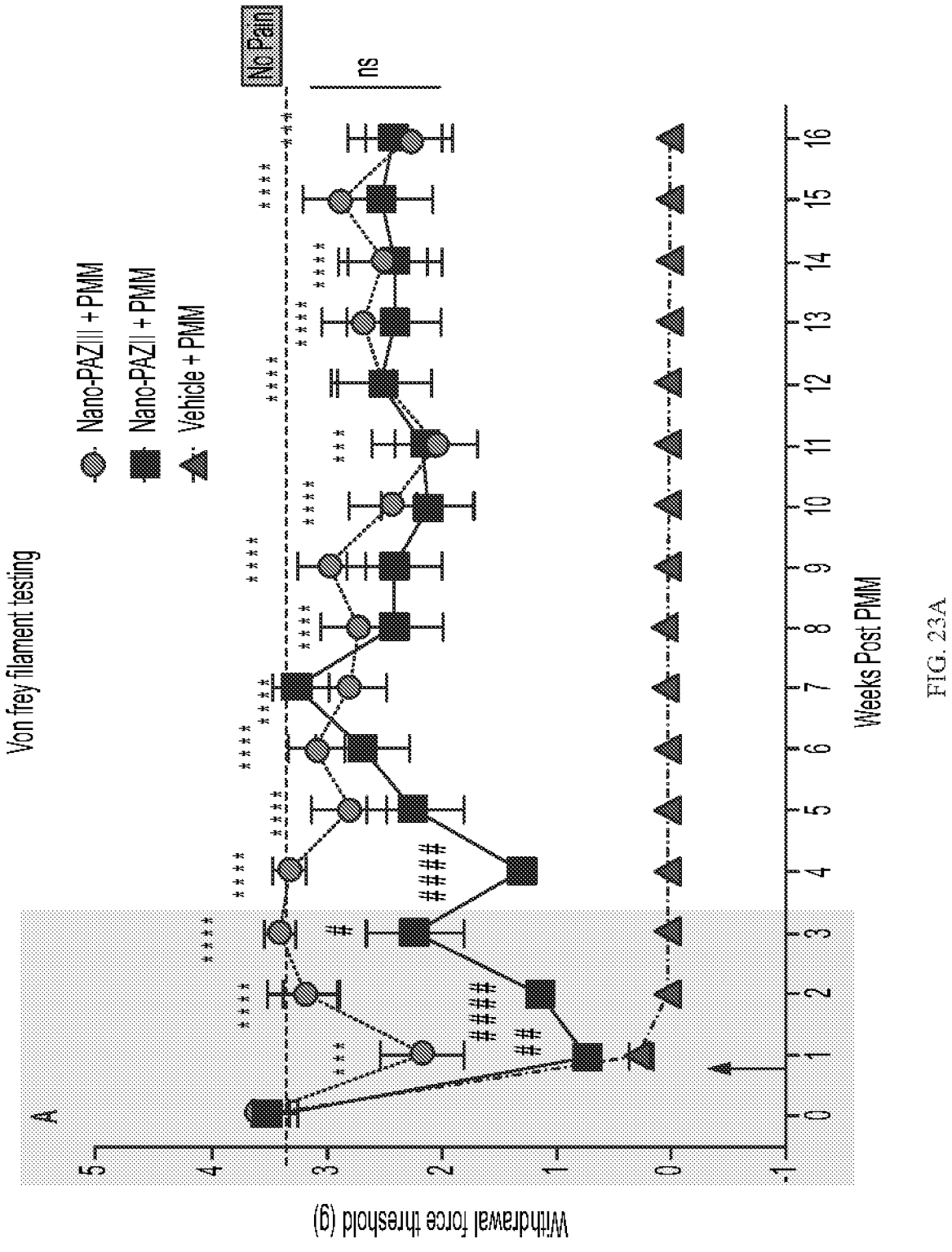
Figure 23B:
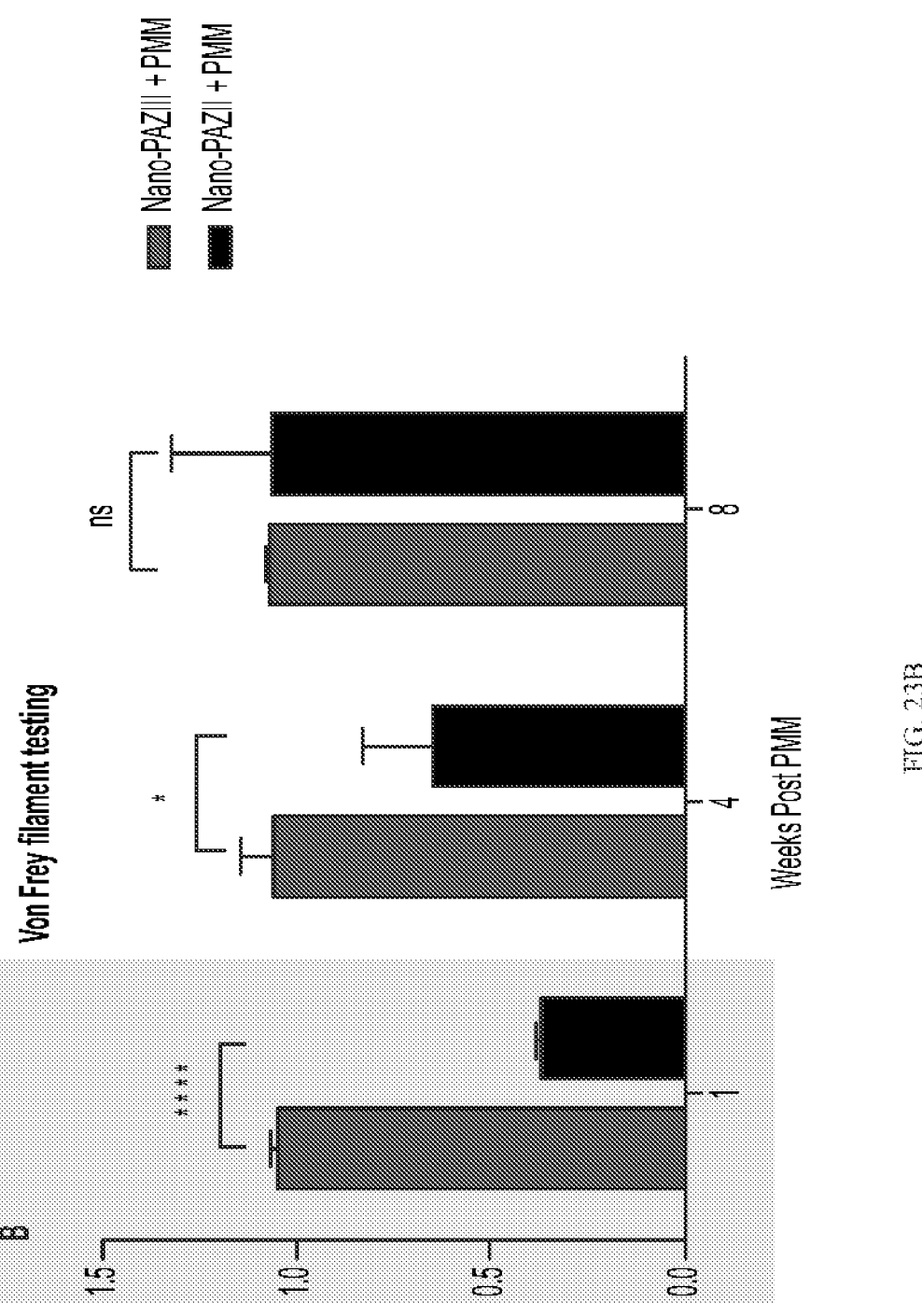

FIGS. 23A-B compares the inflammatory pain stage a week after intraarticular (IA) drug injection. FIG. 23A shows a comparison of nano-PAZII and nano-PAZIII on mechanical allodynia after a single intraarticular (IA) injection (65 µg/knee). *p<0.001, **p<0.001 compared between Nano-PAZIII and vehicle (Veh, nanoparticle) treatment among mice that underwent PMM. #p<0.05, ##p<0.01, ###p<0.001, ####p<0.0001 compared between Nano-PAZIII and Nano-PAZII treatment among mice that underwent PMM. The arrow indicates the time of a single IA treatment with Nano-PAZII or Nano-PAZIII, NS, not significant; PMM=partial medial meniscectomy. FIG. 23B shows the differences in the mechanical allodynia comparing the drug efficacy of nano-PAZII and III, immediately after a single IA drug treatment. The difference in the drug efficacy on pain reduction is gradually getting smaller. No significance is found in the drug efficacy on pain between nano-PAZII and nano-PAZIII after 6 weeks post-IA treatment.

Figure 24A:
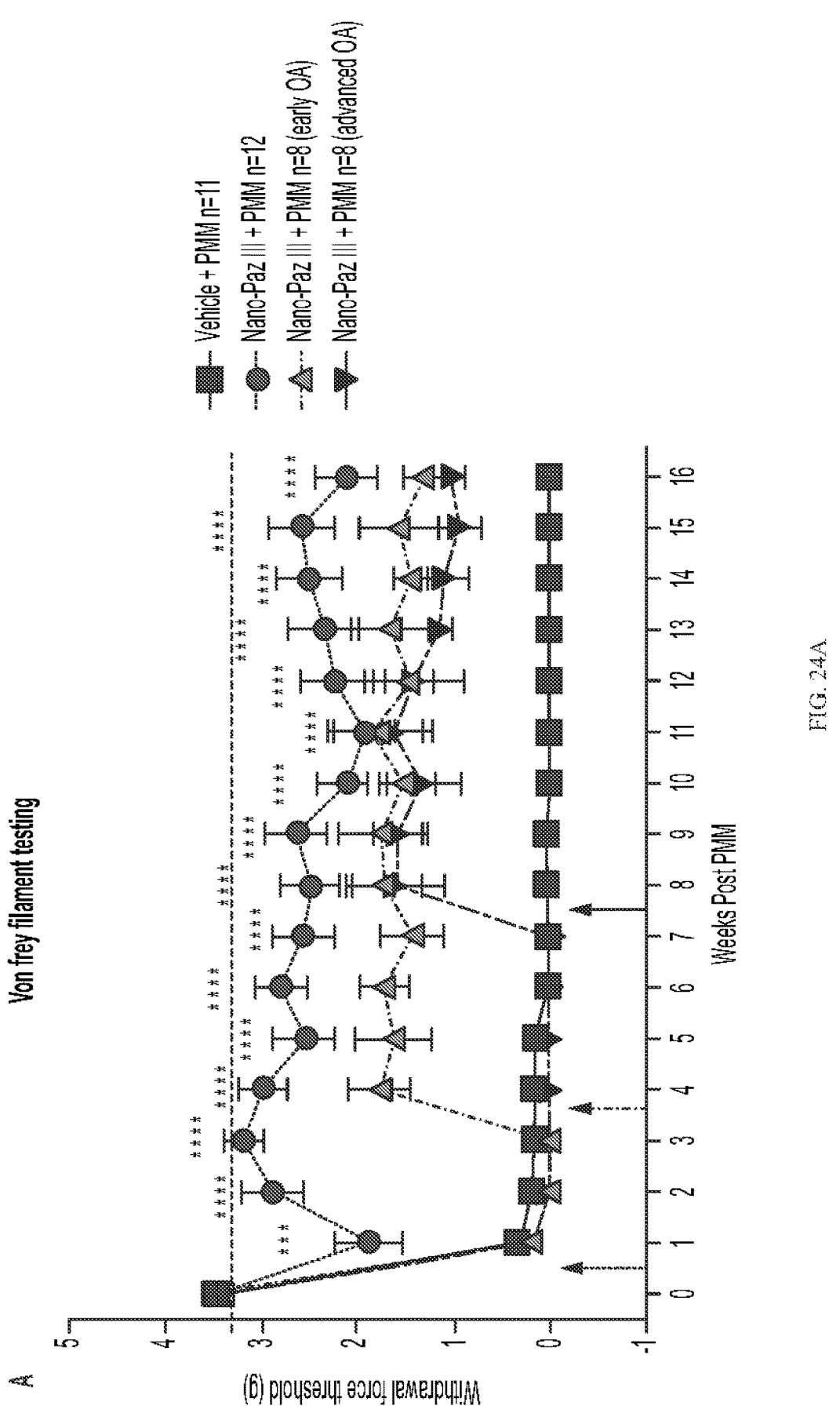
Figure 24B:
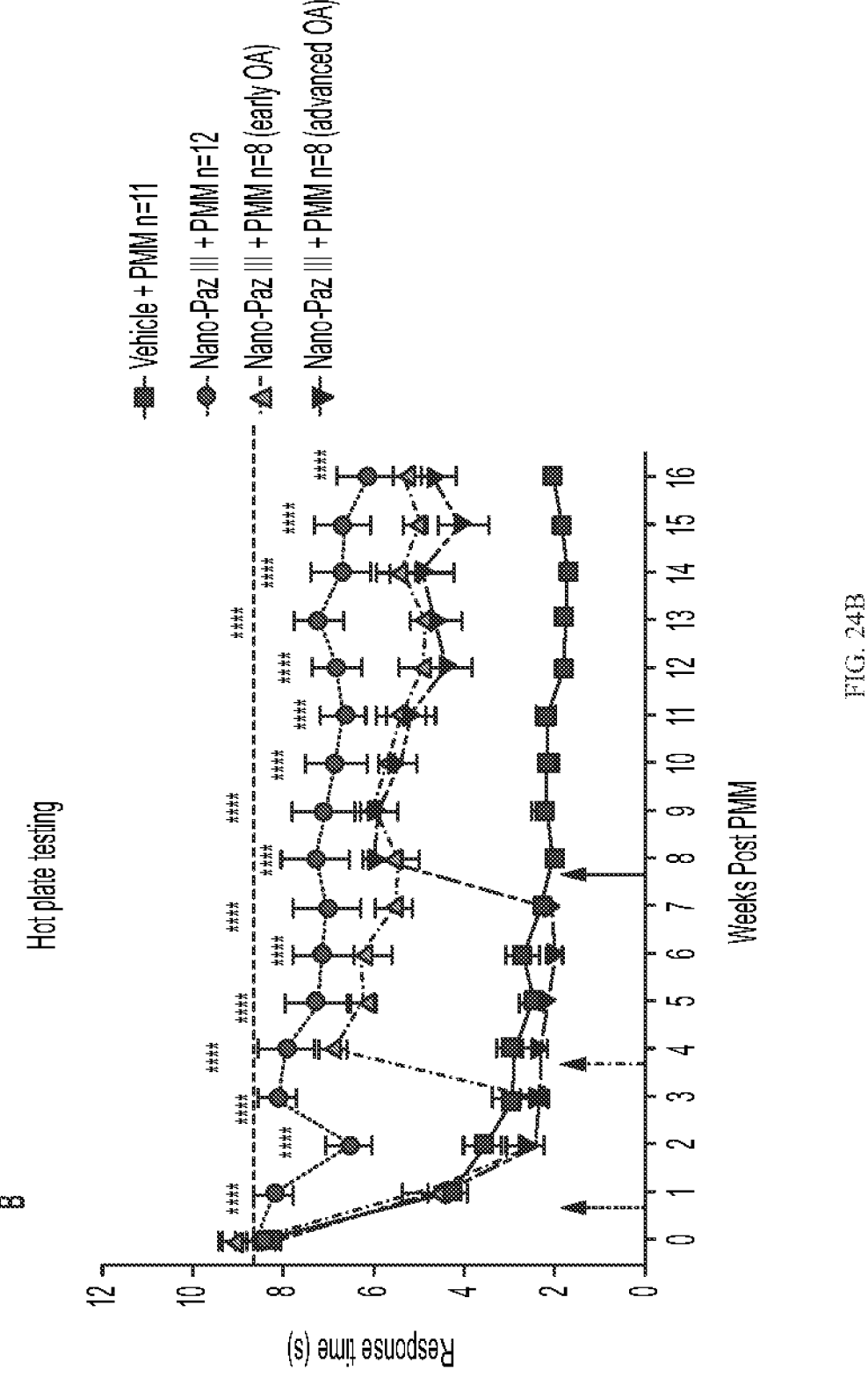

FIGS. 24A-B show that mechanical allodynia (FIG. 24A) or temperature sensitivity (FIG. 24B) after a single intraarticular (IA) injection of nano-PAZIII (65 µg/knee) therapy during the OA disease progression: inflammatory pain stage (within a week post-injury, first arrow), early OA (4 weeks post-PMM, second arrow) or later OA stages (8 weeks post-PMM, third arrow). Rapid pain reduction shown after IA injection. *p<0.05, compared to Vehicle+PMM. *p<0.001, **p<0.001 compared between groups with or without Nano-PAZIII treatment among mice that underwent PMM surgery.

Figures 25A, 25B:
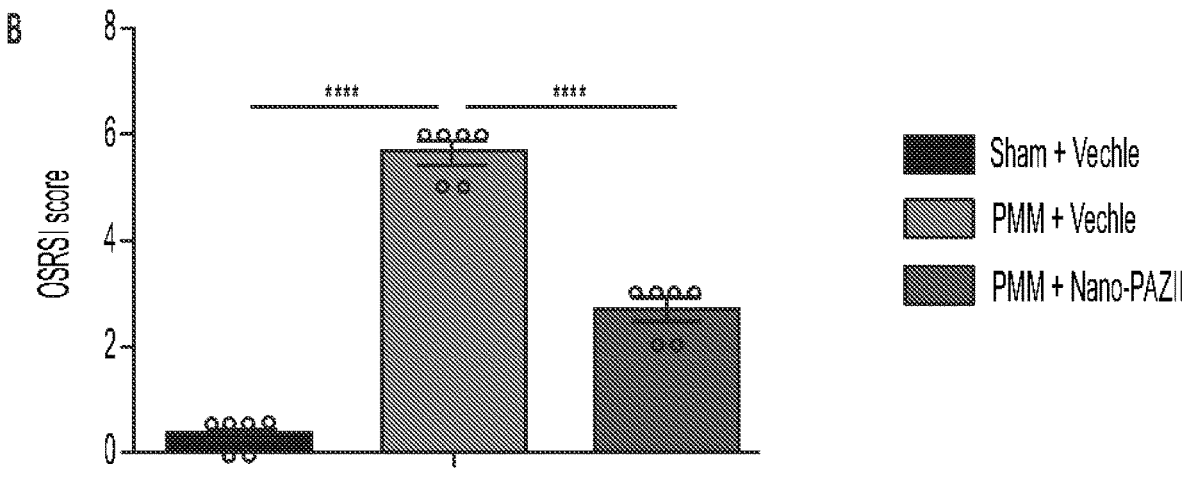

FIGS. 25A-B show the results of a single intraarticular (IA) injection of Nano-Paz II (65 µg/knee) at the time of j oint injury in animals that were sacrificed at 16 weeks post-PMM. FIG. 25A shows the histopathological analyses by Safranin O-staining demonstrating excellent cartilage protection. FIG. 25B shows the quantitation of pathology by OASRSI score, *p<0.001, **p<0.0001. PMM=partial medial meniscectomy.

Figure 26A:
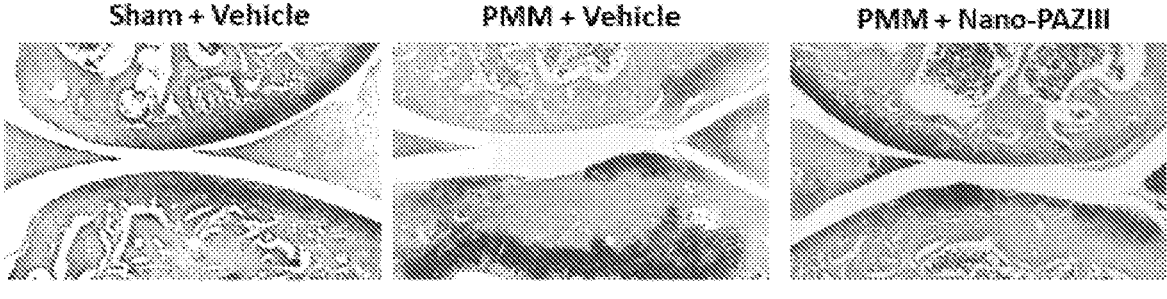
Figure 26B:
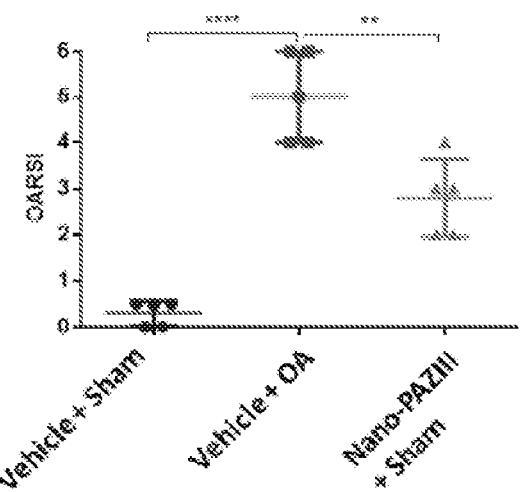

FIGS. 26A-B show the results of a single intraarticular (IA) injection of Nano-PazIII (65 µg/knee) at the time of j oint injury in animals that were sacrificed at 16 weeks post-PMM. FIG. 26A shows the histopathological analyses by Safranin O-staining demonstrating excellent cartilage protection. FIG. 25B shows the quantitation of pathology by OASRSI score, *p<0.001, **p<0.0001. PMM=partial medial meniscectomy.

Figure 27A:
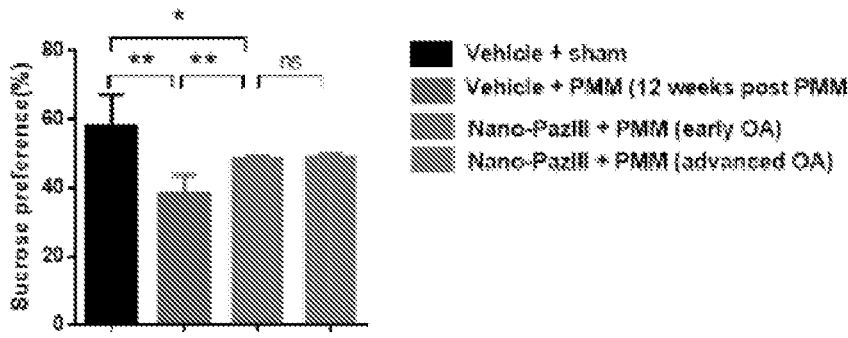
Figure 27B:
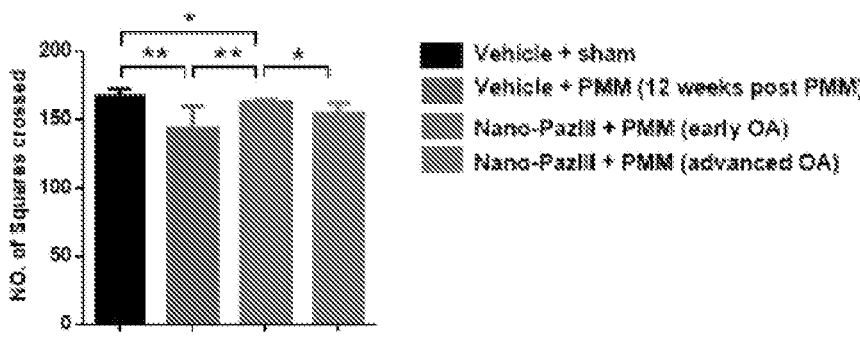

FIGS. 27A-B show reduced symptoms of depression by Nano-PAZIII treatment. The sucrose preference test (SPT) is used as in indicator of anhedonia (FIG. 27A) and the open field test is used as a common measure of exploratory behavior to assess the degree of depression level (FIG. 27BB) were carried out with and without a single intraarticular (IA)nano-PAZIII treatment at week 16 post-PMM (PMM=partial medial meniscectomy). Data are expressed as mean±S.E.M. Statistical analysis was conducted using the unpaired t-test. *p<0.05, p<0.01, *p<0.001 making comparisons between Nano-PAZIII and vehicle (nanoparticles) treatment in mice with PMM. Nano-PAZIII treatment significantly increases the sucrose preference ratio in mice with PMM. There is no difference in the sucrose preference ratio between early OA and advanced OA group mice. A single IA Nano-PAZIII treatment also significantly increased the number of square crossings in the PMM mice (FIG. 27B), demonstrating reduced levels of depression.

DETAILED DESCRIPTION

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

As used in the specification and the appended claims, the singular forms "a," "an" and "the" include plural referents unless the context clearly dictates otherwise.

The word "or" as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "subject" refers to the target of administration, e.g., a human. Thus, the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, the subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for osteoarthritis or depression or anxiety associated with osteoarthritis, a joint injury, or a joint disease, such as, for example, prior to the administering step.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. For example, the disease, disorder, and/or condition can be osteoarthritis or depression or anxiety associated with osteoarthritis.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition. In some aspects, administration can be an intraarticular injection.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene 9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form, which may be supplied on computer readable memory device or downloaded from an internet website, or as recorded presentation. Instructions can comprise one or multiple documents, and are meant to include future updates.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions that can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "stable," as used herein, refers to compositions that are not substantially altered when subjected to conditions to allow for their production, detection, and, in certain aspects, their recovery, purification, and use for one or more of the purposes disclosed herein.

"Inhibit," "inhibiting" and "inhibition" mean to diminish or decrease an activity, level, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

"Nanoparticle," as used herein, refers to a solid nanoparticle entity formed by physical aggregation or noncovalent chemical association (e.g., through one or more noncovalent bonds) of two or more molecular entities. In some aspects, a Pazopanib or a derivative thereof is encapsulated within the nanoparticle. "Pazopanib nanoparticle," as used herein, refers to a solid nanoparticle encapsulating Pazopanib or a derivative thereof with a polyethylene glycol and includes for example, nanoparticles in which the Pazopanib or a derivative thereof is at least partially encapsulated by polyethylene glycol. "Pazopanib nanoparticle" also includes nanoparticles in which the Pazopanib or a derivative thereof and polyethylene glycol is self-assembled through physical aggregation or noncovalent chemical association, in addition to nanoparticles that have a micelle or micelle-like structure. In general, the disclosed nanoparticles have a size ranging from about 200 nm to about 2,000 nm, e.g., from about 200 nm to about 1,000 nm, or from about 200 nm to about 500 nm. Particle size can be determined using methods known in the art, e.g., light scattering or zeta potential measurements. Particle size, as referred to herein, refers to the mean or average particle size of a given Pazopanib nanoparticle sample.

The term "mass ratio," as used herein, refers to the mass of one substance (S1) relative to the mass of another substance (S2), where both masses have identical units (e.g., grams), expressed as S1:S2. For a substance such as water with a density of about 1 mg/mL, it is understood that reference to a volume of water (e.g., in mL) is equivalent to mass (e.g., in units of mg).

"PLGA" as used herein refers to a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation of PLGA can be adjusted by altering the lactic acid-glycolic acid ratio. In some aspects, PLGA to be used in accordance with the present invention can be characterized by a lactic acid: glycolic acid ratio of approximately 85:15, approximately 75:25, approximately 60:40, approximately 50:50, approximately 40:60, approximately 25:75, or approximately 15:85. Preferably, the lactic acid:glycolic acid ratio is approximately 50:50.

As used herein, the terms "PEG", "polyethylene glycol", or "poly(ethylene glycol)" as used herein refers to any water soluble poly(ethylene oxide), and includes molecules comprising the structure $-(CH_2CH_2O)_n-$ where n is an integer from 2 to about 800. A commonly used PEG is end-capped PEG, wherein one end of the PEG is capped with a relatively inactive group such as an alkoxy while the other end is a hydroxyl group that may be further modified. An often-used capping group is methoxy and the corresponding end-capped PEG is often denoted mPEG. The notion PEG is often used instead of mPEG. Specific PEG forms of the invention are branched, linear, forked PEGs, and the like and the PEG groups are typically polydisperse, possessing a low polydispersity index of less than about 1.05. The PEG moieties of the invention will, for a given molecular weight, typically consist of a range of ethylene glycol (or ethylene-oxide) monomers. For example, a PEG moiety of molecular weight 2000 Da will typically consist of 43±10 monomers, the average being around 43 monomers. The term "PEGylated" refers to the covalent attachment of PEG to another molecule, such as any of the peptides disclosed herein.

Genomic studies revealed that vegf expression is an osteoarthritis (OA) marker that is strongly associated with painful OA progression in humans (Ji T J, et al. Advance Science 2021, 2100351). However, multiple VEGF ligands have been shown to have redundant and compensatory roles (Schrodt M V and Ankrum J A. New & Views, Nature Biomedical Engineering 2022, 6:6-7) that may contribute to OA progression and pain. Thus, it was suggested that targeting the receptors on which ligands converge may be more effective than targeting individual ligands. Different pathologic roles for VEGFRs have been shown during OA progression: VEGFR-1 (known as Flt1) is the major driver of joint pain transmission, and VEGFR-2 (known as Flk1) is primarily responsible for cartilage tissue degeneration in OA (Dominick K L, et al. J Rheumatol. 2006; 33(2):348-354; Kotlarz H, et al. Arthritis Rheum. 2009 60, 3546; and Wong S W, et al. Advanced Science 2020 7, 2001066). The role of Flt1 in controlling pain was not limited to knee OA pain. Recent results demonstrated fast pain-reliving action by blocking the Flt1 pathway in disc degeneration-induced low back pain (LBP) (United States Bone and Joint Initiative. The Burden of Musculoskeletal Diseases in the United States (BMUS). In: In. Fourth ed. Rosemont, IL. 2018: Available at boneandjointburden.org/fourth-edition. Accessed Jun. 12, 2019). Thus, simultaneous inhibition of Flt1 may benefit knee OA pain as well as musculoskeletal pain disorder, the most common and serious chronic pain complaint among veterans. As described herein, simultaneous inhibition of Flt1 and Flk1 using Pazopanib, an FDA-approved small molecule inhibitor for both Flt1 and Flk1, was investigated and showed dual effects: (i) rapid joint pain reduction; and (ii) inhibition of cartilage degeneration that gradually promotes cartilage regeneration in the established OA model.

Roles for VEGF/VEGFR signaling in joint pathology and pain transmission. A feature of OA is the increase in vascular endothelial growth factor (VEGF) levels and new blood vessel formation in the joints, both of which correlate with OA pain (United States Bone and Joint Initiative. The Burden of Musculoskeletal Diseases in the United States (BMUS). In: In. Fourth ed. Rosemont, IL. 2018: Available at boneandjointburden.org/fourth-edition. Accessed Jun. 12, 2019; Stanishewski M and Zimmermann B. Fed Pract. 2015. 32(Supp 12): 21S; Dominick K L, et al. J Rheumatol. 2006; 33(2):348-354; Kotlarz H, et al. Arthritis Rheum. 2009 60, 3546; Wong S W, et al. Advanced Science 2020 7, 2001066; Wong S W, et al. Nature Biomedical engineering 2022, 6:54; and Das V, et al. Gene Reports 2018, 11:94-100). VEGF-family ligands (VEGF-A~E) signal mainly via three receptor tyrosine kinases, VEGFR1 (Flt1), VEGFR2 (Flk1) and VEGFR3 (Flt4). VEGF-A activates both Flt1 and Flk1; VEGF-B and placental growth factor (PlGF) activate Flt1; VEGF-E (encoded by viruses) exclusively activates Flk1 (Das et al. Gene. 2018, 20 (655): 1-12); and VEGF-C and VEGF-D activate Flt1 and Flt4. The results using human joint tissues showed that ligands for Flt1 and Flk1 (but not Flt4) are significantly increased in joint tissues from OA patients, showing a pathologic role of Flt1 and Flk1 in OA.

Figure 1:
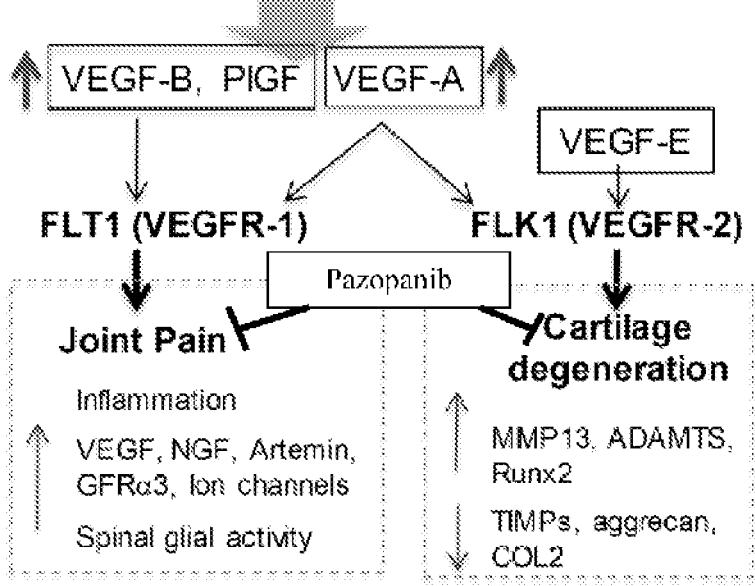
FIG. 1 shows a schematic of the roles Flt1 and Flk1 play in joint pain and cartilage degeneration through VEGF receptor-1 (VEGFR-1) and VEGF receptor-2 (VEGFR-2), respectively.

Redundant and compensatory roles among Flt1 ligands (VEGF-B, P1GF, VEGF-A) have been reported (Im H J, et al. (2010). Arthritis Rheum 62:2995) and may contribute to OA progression and pain. Thus, targeting the receptor that these ligands converge upon may be more efficacious than targeting individual ligands. Results suggest that intra-articular (IA) injection of VEGF into the knee joint leads to OA-like joint pathology, inhibition of VEGF signaling decreases OA progression. Further, VEGF-A, a ligand that activates both Flt1 and Flk1, is involved in cartilage degeneration and OA pain. For example, Selvaraj (Knights C B, et al. Pain. 2012 February; 153 (2):281-92) showed a role for Flt1 in cancer pain. Collectively, Flk1 protects joints from cartilage degeneration while Flt1 is involved in the generation of OA pain (FIG. 1). The findings disclosed herein show that targeting both Flt1 and Flk1 can elicit: (i) rapid relief of joint pain and; (ii) slow down disease progression, and restore joint function.

Local treatment using intraarticular (IA) administration of drugs can be used for OA treatment to minimize potential adverse effects that are commonly associated with systemic drug exposure. However, to meet the requirement of local injection in clinical settings, it is important to reduce the frequency of drug injections. Described herein are nanotechnology-based formulations of pazopanib (referred as 'nano-PAZ') developed to provide prolonged and sustained drug efficacy to control pain and OA disease progression simultaneously for at least 16 weeks or longer by a single intraarticular (IA) injection using an OA model. The nano-PAZ drug formulation disclosed herein can be useful as OA disease-modifying drug (OADMD) that can be translatable to clinical settings, and can be used as an anti-depression drug for OA-associated depressive disorders.

Compositions

Disclosed herein are nanoparticles comprising Pazopanib or a derivative thereof encapsulated by the copolymer poly (lactic-co-glycolic acid) (PLGA). Disclosed herein are nanoparticles consisting of Pazopanib or a derivative thereof encapsulated by the copolymer poly(lactic-co-glycolic acid) (PLGA).

Also disclosed herein are nanoparticle comprising or consisting of Pazopanib or a derivative thereof encapsulated by poly(ethylene glycol)-b-poly(c-caprolactone) (PEG-b-PCL).

In some aspects, the nanoparticles can have a diameter of less than 1000 nm. In some aspects, the nanoparticle can have a diameter of from about 500 nm to about 600 nm. In some aspects, the nanoparticle can have a diameter of from about 400 nm to about 500 nm. In some aspects, the nanoparticle can have a diameter of from about 300 nm to about 400 nm. In some aspects, the nanoparticle can have a diameter of from about 200 nm to about 300 nm. In some aspects, the nanoparticle can have a diameter of from about 100 nm to about 200 nm. In some aspects, the nanoparticle can have a diameter of from about 50 nm to about 100 nm. In some aspects, the nanoparticle can have a diameter of from about 600 nm to about 700 nm. In some aspects, the nanoparticle can have a diameter of from about 700 nm to about 800 nm. In some aspects, the nanoparticle can have a diameter of from about 800 nm to about 900 nm. In some aspects, the nanoparticle can have a diameter of from about 900 nm to about 1000 nm.

In some aspects, the nanoparticles of the invention can include about 10 to about 99 weight %, or about 20 to about 80 weight %, about 40 to about 80 weight %, or about 30 to about 50 weight %, or about 70 to 90 weight % of PLGA.

In some aspects, PLGA can have a number average molecular weight of about 5 to about 15 kDa, or about 5 to about 12 kDa. In some aspects, PLGA can have a number average molecular weight of about 8 to about 12 kDa.

In some aspects, the nanoparticles can comprises about 2 to about 25 weight percent of the Pazopanib or a derivative thereof. In some aspects, the nanoparticles can comprises about 1 to about 25 weight percent of the Pazopanib or a derivative thereof. In some aspects, the nanoparticles can comprises about 3 to about 25 weight percent of the Pazopanib or a derivative thereof. In some aspects, the nanoparticles can comprises about 4 to about 25 weight percent of the Pazopanib or a derivative thereof. In some aspects, the nanoparticles can comprises about 5 to about 25 weight percent of the Pazopanib or a derivative thereof. In some aspects, the nanoparticles can comprises about 6 to about 25 weight percent of the Pazopanib or a derivative thereof. In some aspects, the nanoparticles can comprises about 7 to about 25 weight percent of the Pazopanib or a derivative thereof. In some aspects, the nanoparticles can comprises about 8 to about 25 weight percent of the Pazopanib or a derivative thereof. In some aspects, the nanoparticles can comprises about 9 to about 25 weight percent of the Pazopanib or a derivative thereof. In some aspects, the nanoparticles can comprises about 10 to about 25 weight percent of the Pazopanib or a derivative thereof. In some aspects, the nanoparticles can comprises about 11 to about 25 weight percent of the Pazopanib or a derivative thereof. In some aspects, the nanoparticles can comprises about 12 to about 25 weight percent of the Pazopanib or a derivative thereof. In some aspects, the nanoparticles can comprises about 13 to about 25 weight percent of the Pazopanib or a derivative thereof. In some aspects, the nanoparticles can comprises about 14 to about 25 weight percent of the Pazopanib or a derivative thereof. In some aspects, the nanoparticles can comprises about 15 to about 25 weight percent of the Pazopanib or a derivative thereof In some aspects, the nanoparticles can comprises about 16 to about 25 weight percent of the Pazopanib or a derivative thereof. In some aspects, the nanoparticles can comprises about 17 to about 25 weight percent of the Pazopanib or a derivative thereof. In some aspects, the nanoparticles can comprises about 18 to about 25 weight percent of the Pazopanib or a derivative thereof. In some aspects, the nanoparticles can comprises about 19 to about 25 weight percent of the Pazopanib or a derivative thereof. In some aspects, the nanoparticles can comprises about 20 to about 25 weight percent of the Pazopanib or a derivative thereof. In some aspects, the nanoparticles can comprises about 21 to about 25 weight percent of the Pazopanib or a derivative thereof. In some aspects, the nanoparticles can comprises about 22 to about 25 weight percent of the Pazopanib or a derivative thereof. In some aspects, the nanoparticles can comprises about 23 to about 25 weight percent of Pazopanib or a derivative thereof. In some aspects, the nanoparticles can comprises about 24 to about 25 weight percent of the Pazopanib or a derivative thereof. In some aspects, the nanoparticles can comprises about 25 to about 30 weight percent of the Pazopanib or a derivative thereof. In some aspects, the nanoparticles can comprises about 30 to about 35 weight percent of the Pazopanib or a derivative thereof. In some aspects, the nanoparticles can comprises about 35 to about 40 weight percent of the Pazopanib or a derivative thereof. In some aspects, the nanoparticles can comprises about 45 to about 50 weight percent of the Pazopanib or a derivative thereof.

In some aspects, the nanoparticles can be pegylated. In some aspects, the nanoparticles can further comprise a peglyated lipid.

In some aspects, the ratio of lactic acid to glycolic acid can be selected to optimize for various parameters such as water uptake, therapeutic agent (Pazopanib or a derivative thereof) release and/or polymer degradation kinetics can be optimized.

In some aspects, the ratio of PLGA to Pazopanib or a derivative thereof is approximately 1:1. In some aspects, the ratio of PLGA to Pazopanib or a derivative thereof is approximately 2:1. In some aspects, PLGA and Pazopanib or a derivative thereof to be used in accordance with the present invention can be characterized by a PLGA: Pazopanib or derivative thereof ratio of approximately 4:1, 3:1, or 2:1.

In some aspects, the mass ratio of Pazopanib or a derivative thereof to PLGA is approximately 1:1. In some aspects, the mass ratio of Pazopanib or a derivative thereof to PLGA is approximately 1:2. In some aspects, the mass ratio of Pazopanib or a derivative thereof to PLGA is from about 300:1 to about 1.1. In some aspects, the mass ratio of Pazopanib or a derivative thereof to PLGA is from about 1:300 to about 1:5. In some aspects, the mass ratio of Pazopanib or a derivative thereof to PLGA is from about 1:50 to 1:10. In some aspects, the mass ratio of Pazopanib or a derivative thereof to PLGA is from about 1:20.

In some aspects, the mass ratio of Pazopanib or a derivative thereof to PLGA is approximately 1:1. In some aspects, the mass ratio of Pazopanib or a derivative thereof to PLGA is approximately 2:1. In some aspects, the mass ratio of Pazopanib or a derivative thereof to PLGA is from about 1:300 to about 1.1. In some aspects, the mass ratio of Pazopanib or a derivative thereof to PLGA is from about 300:1 to about 5:1. In some aspects, the mass ratio of Pazopanib or a derivative thereof to PLGA is from about 50:1 to 10:1. In some aspects, the mass ratio of Pazopanib or a derivative thereof to PLGA is from about 20:1.

In some aspects, the nanoparticles can further comprise a cryo-protective agent. In some aspects, the cryo-protective agent can be present in an amount of about 15 wt % or less. In some aspects, the cryo-protective agent can be present in an amount of from about 5 wt % to about 15 wt %. In some aspects, the cryo-protective agent can be sucrose or trehalose.

In some aspects, the nanoparticle can further contains a positively charged molecule. In some aspects, the nanoparticle can further contains a positively charged lipid.

Also disclosed herein are composition comprising two or more nanoparticles described herein.

Methods of Treatment

Disclosed herein are methods of inhibiting cartilage degeneration in a subject. In some aspects, the methods can comprise administering to the subject in need thereof a therapeutically effective amount of a composition comprising any of the nanoparticle described herein or any of the pharmaceutical compositions described herein.

Disclosed herein are methods of reducing pain or reducing joint pain in a subject. In some aspects, the methods can comprise administering to the subject in need thereof a therapeutically effective amount of a composition comprising any of the nanoparticle described herein or any of the pharmaceutical compositions described herein.

Disclosed herein are methods of protecting cartilage or preventing cartilage degeneration in a subject. In some aspects, the methods can comprise administering to the subject in need thereof a therapeutically effective amount of a composition comprising any of the nanoparticle described herein or any of the pharmaceutical compositions described herein.

Disclosed herein are methods of preventing or reducing or inhibiting pain-associated depression in a subject. In some aspects, the methods can comprise administering to the subject in need thereof a therapeutically effective amount of a composition comprising any of the nanoparticle described herein or any of the pharmaceutical compositions described herein. In some aspects, the depression can be a depression condition or anxiety.

Disclosed herein are methods of reducing spinal activation of NF-kB glial axis in a subject. In some aspects, the methods can comprise administering to the subject in need thereof a therapeutically effective amount of a composition comprising any of the nanoparticle described herein or any of the pharmaceutical compositions described herein.

Disclosed herein are methods of treating osteoarthritis in a subject in need thereof. In some aspects, the methods can comprise administering to the subject in need thereof a therapeutically effective amount of a composition comprising any of the nanoparticle described herein or any of the pharmaceutical compositions described herein.

Disclosed herein are methods of reducing or ameliorating one or more symptoms of osteoarthritis in a subject. In some aspects, the methods can comprise administering to the subject in need thereof a therapeutically effective amount of a composition comprising any of the nanoparticle described herein or any of the pharmaceutical compositions described herein. In some aspects, the one or more symptoms of osteoarthritis can be pain. Examples of symptoms of osteoarthritis include but are not limited to joint stiffness, decreased range of motion (flexibility) and swelling. Osteoarthritis occurs when the protective cartilage that cushions the ends of bones wears down over time. In some aspects, osteoarthritis can damage or effect any joint. In some aspects, the joint can be in the hands, knees, hips, spine, feet, neck or shoulder.

Disclosed herein are methods of treating a joint disease in a subject in need thereof. In some aspects, the methods can comprise administering to the subject in need thereof a therapeutically effective amount of a composition comprising any of the nanoparticle described herein or any of the pharmaceutical compositions described herein. In some aspects, the joint disease can be a degenerative joint disease. In some aspects, the degenerative joint disease can be osteoarthritis.

Disclosed herein are methods of treating a joint condition in a subject in need thereof. In some aspects, the methods can comprise administering to the subject in need thereof a therapeutically effective amount of a composition comprising any of the nanoparticle described herein or any of the pharmaceutical compositions described herein. In some aspects, the joint condition can be a joint injury. In some aspects, the joint injury can be a traumatic injury or a post-operative injury. In some aspects, the joint injury can be a repetitive strain injury.

In any of the methods disclosed herein, the subject has or was diagnosed with osteoarthritis prior to the administering step.

In any of the methods disclosed herein, the administration of any of the nanoparticle described herein or any of the pharmaceutical compositions described herein can be via intraarticular administration.

In any of the methods disclosed herein, the methods can further comprising administering mesenchymal stem cells (MSCs) to subject in combination with one or more of the nanoparticles or pharmaceutical compositions disclosed herein. For example, disclosed herein are methods comprising administering any of the nanoparticle described herein or any of the pharmaceutical compositions described herein in combination with MSCs to a subject. In some aspects, the MSCs can be administered before, after, or during the administration of any of the nanoparticle described herein or any of the pharmaceutical compositions described herein.

Disclosed herein are methods of enhancing tissue regeneration in a subject in need thereof. In some aspects, the methods can comprise administering to the subject in need thereof a therapeutically effective amount of a composition comprising any of the nanoparticles described herein or any of the pharmaceutical compositions described herein and mesenchymal stem cells. In some aspects, the subject has or was diagnosed with osteoarthritis prior to the administering step. In some aspects, the administration of the composition comprising any of the nanoparticle described herein or any of the pharmaceutical compositions can be by intraarticular administration. In some aspects, the administration of the MSCs can be by intraarticular administration.

Pharmaceutical Compositions

As disclosed herein, are pharmaceutical compositions, comprising one or more of the nanoparticles described herein. Also disclosed herein are composition comprising two or more nanoparticles described herein. As disclosed herein, are pharmaceutical compositions, comprising Pazopanib or a derivative thereof encapsulated in a nanoparticle and a pharmaceutical acceptable carrier described herein. In some aspects, compositions can be formulated for oral or parental administration. In some aspects, the parental administration can intravenous, subcutaneous, intramuscular or direct injection. In some aspects, compositions can be formulated intraarticular administration. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

In some aspects the concentration of Pazopanib or a derivative thereof encapsulated in the nanoparticles is from about 0.5 mg/ml-15.0 mg/ml. In some aspects the concentration of Pazopanib or a derivative thereof encapsulated in the nanoparticles is from about 1.0 mg/ml — 7.0 mg/ml. In some aspects the concentration of Pazopanib or a derivative thereof encapsulated in the nanoparticles is about 6 mg/ml. In some aspects the concentration of Pazopanib or a derivative thereof encapsulated in the nanoparticles is about 0.5 mg/ml.

The compositions can be administered directly to a subject. Generally, the compositions can be suspended in a pharmaceutically acceptable carrier (e.g., physiological saline or a buffered saline solution) to facilitate their delivery. Encapsulation of the compositions in a suitable delivery vehicle (e.g., implantable devices) may increase the efficiency of delivery.

The compositions can be formulated in various ways for parenteral or nonparenteral administration. Where suitable, oral formulations can take the form of tablets, pills, capsules, or powders, which may be enterically coated or otherwise protected. Sustained release formulations, suspensions, elixirs, aerosols, and the like can also be used.

In some aspects, the nanoparticles and pharmaceutical formulations described herein may have controlled release properties, e.g., may be capable of delivering an amount of active agent to a subject e.g., to a specific site in a subject and/or over an extended period of time, e.g., over 1 day, 1 week or more. In some aspects, nanoparticles of the invention immediately release (e.g., over about 1 minute to about 30 minutes), less than about 2%, less than about 5%, or less than about 10% of Pazopanib or a derivative thereof, for example when placed in a phosphate buffer solution at room temperature and/or 37° C.

In some aspects, the nanoparticles and pharmaceutical formulations described herein, may, in some aspects, release pazopanib or a derivative thereof when placed in an aqueous solution, for example, at 25° C. with a rate substantially corresponding to a) from about 0.01 to about 20% of the total pazopanib or a derivative thereof is released after about 1 hour; b) from about 10 to about 50% of the total pazopanib or a derivative thereof is released after about 8 hours; c) from about 30 to about 50% of the total pazopanib or a derivative thereof is released after 12 hours; and d) not less than about 50% of the total pazopanib or a derivative thereof is released after about 24 hours.

In some aspects, the nanoparticles and pharmaceutical formulations described herein, may, in some aspects, release pazopanib or a derivative thereof such that the cumulative release of pazopanib or a derivative thereof can be from about 10% after about immediately to about 1.5 weeks; from about 20% after about 1.5 to 3 about weeks; from about 30% after about 3 to about 6 weeks; from about 40% after about 4.5 to about 9 weeks; from about 50% after about 7 to 12 weeks.

In some aspects, the release rate of pazopanib or a derivative thereof from any of the nanoparticles and pharmaceutical formulations described herein can allow for sustained efficacy 1-60 minutes to more than 1, 2, 3, 4, 5, 6, 7, 8, 9, 10, 11, 12, 13, 14, 15, 16, 17, 18, 19, 20 hours or longer.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

The pharmaceutical compositions as disclosed herein can be prepared for oral or parenteral administration. The pharmaceutical compositions as disclosed herein can be prepared for intraarticular administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. In some aspects, the compositions can be prepared for inferior alveolar administration. Thus, compositions can be prepared for parenteral administration that includes pazopanib or a derivative thereof dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like).

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules.

In some aspects, the pharmaceutical composition can be formulated for oral or intravenous administration or intraarticular administration. In some aspects, the composition can be formulated in a lipid emulsion. In some aspects, any of the compositions, pharmaceutical compositions or nanoparticles disclosed herein can be formulated for intraarticular injection.

Articles of Manufacture

The composition described herein can be packaged in a suitable container labeled, for example, for use as a therapy to treat osteoarthritis or any of the methods disclosed herein. Accordingly, packaged products (e.g., sterile containers containing the composition described herein and packaged for storage, shipment, or sale at concentrated or ready-to-use concentrations) and kits, including at least pazopanib or a derivative thereof as described herein and instructions for use, are also within the scope of the disclosure. A product can include a container (e.g., a vial, jar, bottle, bag, or the like) containing the composition described herein. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compositions can be ready for administration (e.g., present in dose-appropriate units), and may include a pharmaceutically acceptable adjuvant, carrier or other diluent. Alternatively, the compounds can be provided in a concentrated form with a diluent and instructions for dilution.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In some aspects, a treatment regime entails administration once per week, once every two weeks, once every three weeks, once every four weeks, once a month, once every 3 months or once every three to 6 months or once every 6 months to a year.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions disclosed herein employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Any of the nanoparticles or compositions disclosed herein can be administered via one or more routes of administration using one or more of a variety of methods known in the art. As will be appreciated by the skilled artisan, the route and/or mode of administration will vary depending upon the desired results. In some aspects, the routes of administration for antibodies disclosed herein include but are not limited to intravenous, intramuscular, intradermal, intraperitoneal, subcutaneous, or other parenteral routes of administration, for example by injection or infusion. The phrase "parenteral administration" as used herein means modes of administration other than enteral and topical administration, usually by injection, and includes, without limitation, intravenous, intramuscular, intraarterial, intraperitoneal, transtracheal, subcutaneous, subcuticular, intraarticular injection and infusion.

The methods and compositions, including combination therapies, enhance the therapeutic or protective effect, and/or increase the therapeutic effect of another anti-inflammatory agent, therapeutic agent or therapy. Therapeutic and prophylactic methods and compositions can be provided in a combined amount effective to achieve the desired effect, such as inhibiting cartilage degeneration, reducing pain or reducing joint pain, protecting cartilage or preventing cartilage degeneration, preventing or reducing or inhibiting pain-associated depression, reducing spinal activation of NF-kB glial axis and/or reducing or ameliorating one or more symptoms of osteoarthritis, joint disease, joint condition or joint injury. This process may involve contacting the cells with both the nanoparticles disclosed herein and a second therapy. In some aspects, the second therapy can be mesenchymal stem cells. A tissue, tumor, or cell can be contacted with one or more compositions or pharmacological formulation(s) comprising one or more of the agents (i.e., the nanoparticles disclosed herein or a second therapeutic agent), or by contacting the tissue, tumor, and/or cell with two or more distinct compositions or formulations, wherein one composition provides 1) one or more nanoparticles, 2) a second therapeutic agent, or 3) both one or more nanoparticles and a second therapeutic agent. Also, it is contemplated that such a combination therapy can be used in conjunction with surgical therapy, for example, joint replacement surgery.

The terms "contacted" and "exposed," when applied to a cell, are used herein to describe the process by which a therapeutic construct and a second therapeutic agent are delivered to a target cell or are placed in direct juxtaposition with the target cell. To achieve the desired outcome, for example, both agents can be delivered to a cell in a combined amount effective to the desired outcome.

The nanoparticles disclosed herein can be administered before, during, after, or in various combinations relative to a second therapeutic agent or therapy. The administrations may be in intervals ranging from concurrently to minutes to days to weeks. In aspects where the nanoparticles re provided to a patient separately from a second therapeutic agent or therapy, one would generally ensure that a significant period of time did not expire between the time of each delivery, such that the two compounds would still be able to exert an advantageously combined effect on the patient. In such instances, it is contemplated that one may provide a patient with the nanoparticles described herein and the second therapeutic agent or therapy within about 0-60 minutes, 1 to 12 h, 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In some aspects, a course of treatment can last between 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there can be a period of time at which no a second therapeutic agent or therapy is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary. In some aspects, a single treatment may be needed to achieve the desired outcome.

In some aspects, nanoparticles disclosed herein can be administered 1, 2, 3, 4, 5, 6, 7, 8, 9, 10 or more days after surgery. In some aspects, the surgery can be destabilization of the medial meniscus surgery. In some aspects, the surgery can be a type of surgery for the treatment of osteoarthritis. In some aspects, the surgery can be a cartilage replacement surgery (e.g., artificial endoprosthesis) or joint arthroplasty. In some aspects, the surgery can be a tendon repair surgery. In some aspects, the surgery can be a joint replacement. In some aspects, the nanoparticles disclosed herein can be administered one or more times separated by one or more weeks. In some aspects, a second, third, fourth, fifth, and so on, administration of the nanoparticles thereof disclosed herein can be separated by 1, 2, 3, 4, 5, 6, 7, 8, 9, 10, 11, or 12 weeks, 3, 4, 5, 6, 7, 8, 9, 10, 11, or 12 months, or 1 or more years. In some aspects, the nanoparticles disclosed herein can be administered one or more times separated by one or more months. In some aspects, a second, third, fourth, fifth, and so on, administration of the nanoparticles disclosed herein can be separated by 1, 2, 3, 4, 5, 6, 7, 8, 9, 10, 11 or 12 months. In some aspects, the nanoparticles disclosed herein can be administered one or more times separated by a variety of intervals, days, weeks, months, years or any combination thereof.

EXAMPLES

Figure 2:
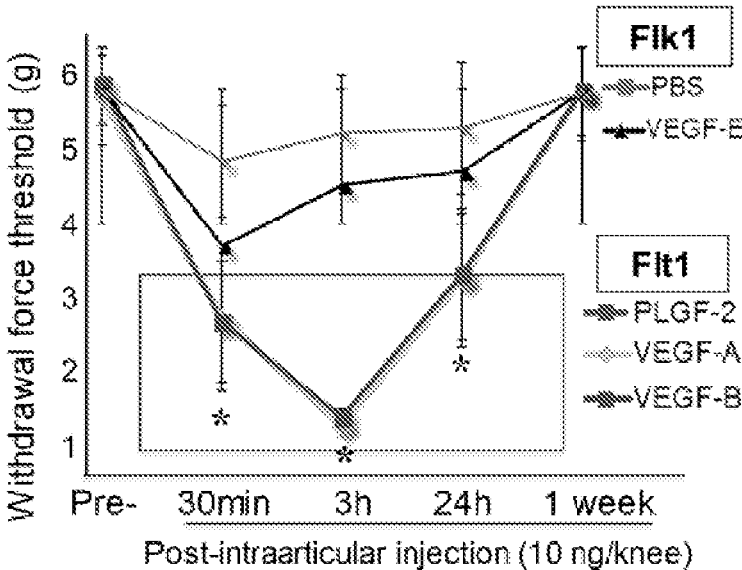
FIG. 2 shows intraarticular injection of selective ligands for Flt1 or Flk1 on mechanical allodynia in mice (n=10/group; *p<0.01).

Example 1: Distinct Roles for Flk1 in Joint Pathology and Flt1 in Pain Transmission VEGF directly modulates the excitability of primary sensory neurons (Knights C B, et al. Pain. 2012 February;

153(2):281-92). The functions of Flt1 in modulating nociception was investigated useing an intraarticular (IA) injection of VEGF ligands selective for either Flt1 or Flk1. Mice showed allodynia within 30 min with ligands for Flt1, but not Flk1 (FIG. 2), demonstrating that Flt1 plays a role in pain transmission.

Using an OA animal model and human tissues, the role of VEGF signaling in OA has been shown to be increased in OA knee (United States Bone and Joint Initiative. The Burden of Musculoskeletal Diseases in the United States (BMUS). In: In. Fourth ed. Rosemont, IL. 2018: Available at boneandjointburden.org/fourth-edition. Accessed Jun. 12, 2019; Stanishewski M and Zimmermann B. Fed Pract. 2015. 32(Supp 12): 21S; Dominick KL, et al. J Rheumatol. 2006; 33(2):348-354; Kotlarz H, et al. Arthritis Rheum. 2009 60, 3546; and Wong S W, et al. Advanced Science 2020 7, 2001066); and that an anti-VEGF Ab or ZD6474, a selective inhibitor of Flk1, reduces OA pathology (Dominick K L, et al. J Rheumatol. 2006; 33(2):348-354; and Kroin J S, et al. Gene. 2016. 10; 591(1): 1-5). Next, outcomes between IA injection of ZD6474 (also known as vandetanib, a selective inhibitor of Flk1, 70 μg/kg, injection frequency: twice per week) and pazopanib (an inhibitor of both Flt1 and Flk1, 70 μg/kg, injection frequency: twice per week) were compared. Twice perweek IA injection of these drugs was started at an inflammatory pain stage (within a week post-surgery) and continued for 12 weeks. After 12 weeks, joints were harvested, histopathological analyses performed, and pathological grading quantified by standard Osteoarthritis Research Society International (OARSI) scoring (1: Healthy, 5: Highly pathologic) (K. O. Vasquez and J. D. Peterson. J Pharmacol Exp Ther 2017, 361:87-98).

Figure 3:
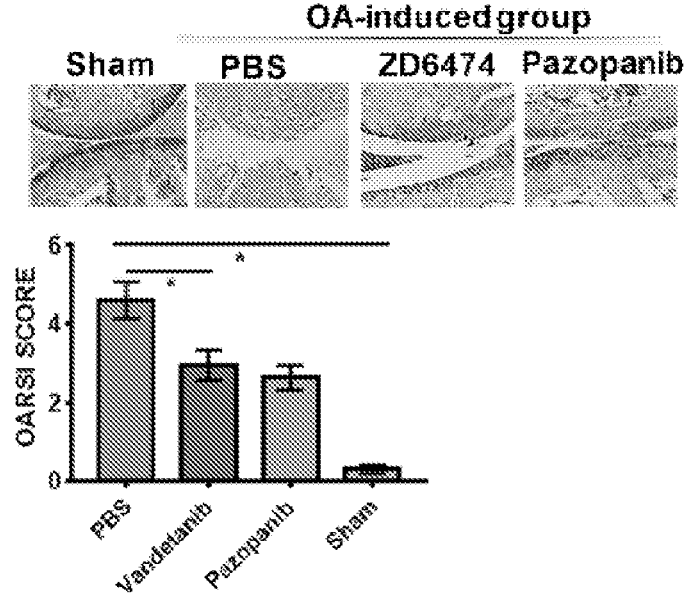
FIG. 3 shows the histology of OA knee joint after treatment for 12 weeks with Pazopanib, ZD6474 or PBS at surgery-induced inflammatory pain stage (n=4 per group). *p<0.05.

Reduction of joint pathology. Targeting Flk1 alone (by ZD6474) or targeting both Flt1 and Flk1 (by pazopanib) preserved cartilage with similar degrees of protection, showing a role for Flk1 in OA disease progression (FIG. 3).

Figure 4:
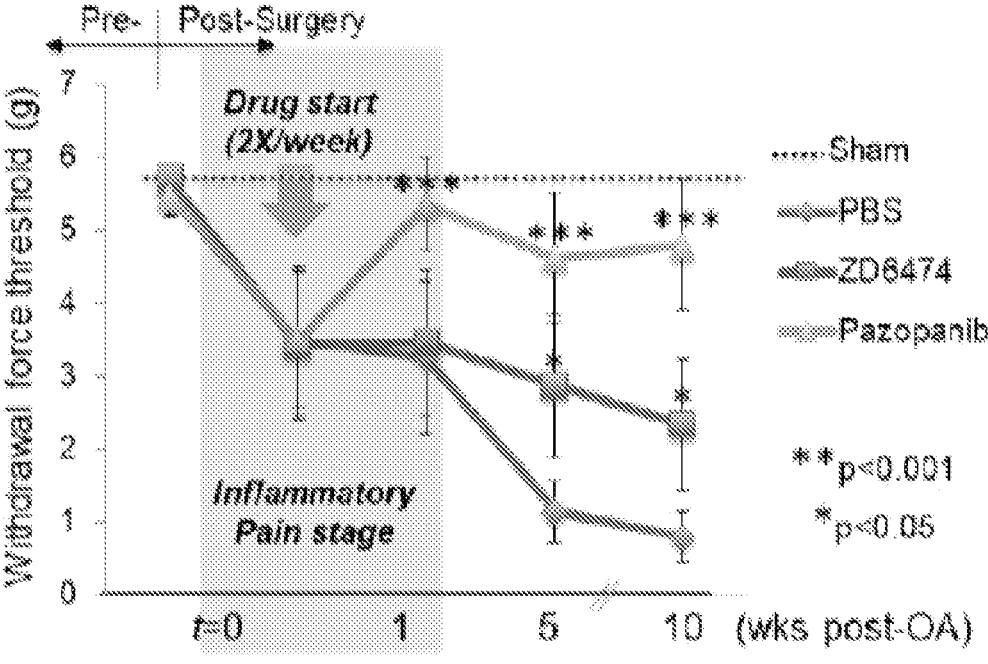
FIG. 4 shows rapid reduction of inflammatory joint pain. Targeting Flk1 alone (by ZD6474), reductions in OA pain were seen 5 weeks after drug injection had started (ZD6474, shown in squares, *p<0.05 vs. PBS), showing that pain reduction by ZD6474 is largely due to decreased disease progression, not due to direct interference with pain pathways. In contrast, rapid joint pain relief was achieved by targeting Flt1 and Flk1 (intraarticular (IA) injection of pazopanib) (triangles; p<0.001 vs. PBS). Indeed, pain reduction by targeting Flt1 and Flk1 (by pazopanib) was far greater than by anti-VEGF Ab treatment.

Rapid and effective reduction of inflammatory joint pain to almost no pain level by pazopanib when treatment began at the inflammatory pain stage. Targeting Flk1 alone (by ZD6474) showed reductions in OA pain as soon as 5 weeks after drug injection had started (FIG. 4, ZD6474 (squares, *p<0.05 vs. PBS), demonstrating that pain reduction by ZD6474 is largely due to decreased disease progression, not due to direct interference with pain pathways. In contrast, rapid joint pain relief was achieved by targeting both Flt1 and Flk1 (IA of pazopanib) (FIG. 4, triangles; p<0.001 vs. PBS). Indeed, pain reduction by targeting Flt1 and Flk1 (by pazopanib) was far greater than by anti-VEGF Ab treatment. These data show that apart from VEGF-A, other Flt1 ligands (VEGF-B or P1GF) are involved in joint hyperalgesia.

Figure 5:
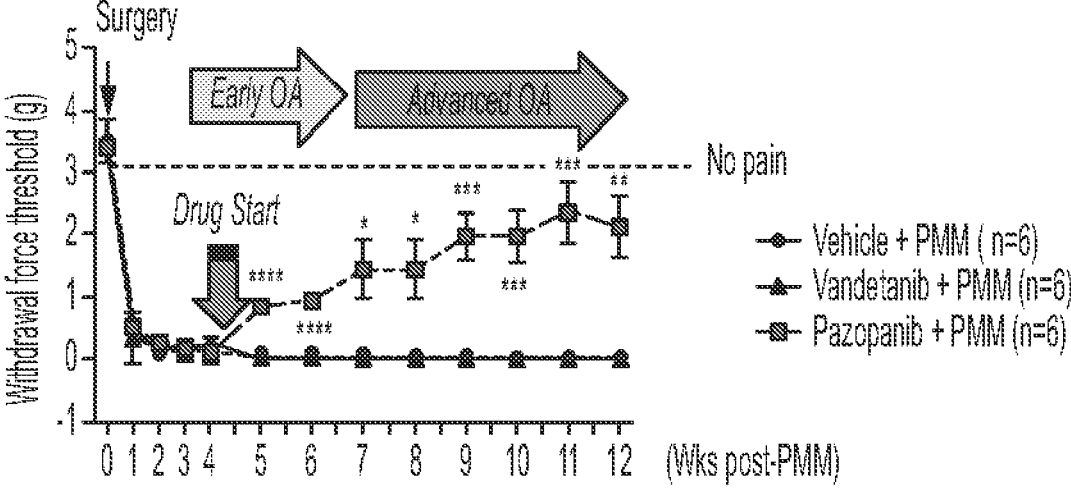
FIG. 5 shows mechanical allodynia measured by von Frey. Drugs are intraarticularly injected (twice/week) at 4 weeks after surgery (early OA stage). *p<0.05; p<0.01; *p<0.001; ****p<0.0001. PMM=partial medial meniscectomy.
Figure 6:
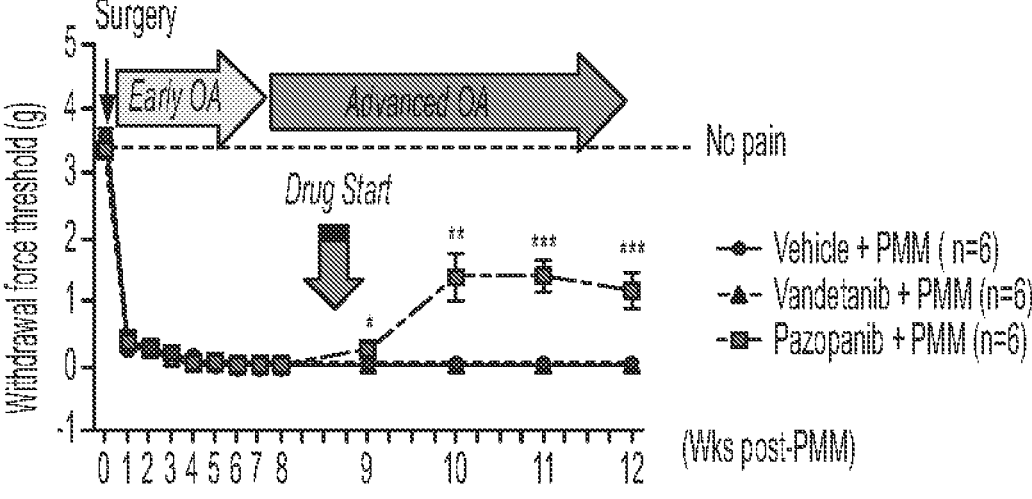
FIG. 6 shows mechanical allodynia measured by von Frey. Drugs are intraarticularly injected (twice/week) at 8 weeks after surgery (advanced OA stage). *p<0.05; p<0.01; *p<0.001. PMM=partial medial meniscectomy.

IA injection of pazopanib (twice per week) reduced joint pain when targeted therapy at early- and advanced OA disease stages. Next, IA injections of drugs (twice/week) was evaluated using animals during either early- or advanced OA joint pain stages. The results show that IA injections with pazopanib (but not ZDD6474) rapidly reduced mechanical allodynia when the drug was injected at the early OA stage (FIG. 5, p<0.0001). Treatments starting at the advanced OA stage also promptly reduced joint pain (FIG. 6, p<0.05). These results demonstrate treatments started at the time of joint injury (FIG. 4) or at early OA stage (FIG. 5) generating rapid and significant pain reduction.

Weekly IA injection of monoclonal antibody (mAb) targeting VEGFR1 (by MF1 mAb) but not VEGFR2 (by DC101 mAb) rapidly reduced joint pain. Monoclonal antibodies (Eli Lilly Co.; administered via IA injection), targeting VEGFR1 and/or VEGFR2 using MF1 (specific to VEGFR1, 5 µg/knee) or DC101 (specific to VEGFR2, 5 µg/knee) or combined MF1+DC101 were evaluated during early- or advanced OA joint pain stages. The results show that IA injection with mAb targeting VEGFR1 (MF1 mAb) but not VEGFR2 (DC101 mAb) rapidly reduced mechanical allodynia and temperature sensitivity (by hot plate testing) indicating pain relief by the drug when injected at the early OA (4 weeks post-PMM) or late OA stage (8 weeks post-PMM). Pain reduction by the combined treatment (MF1+ DC101) was almost the same as treatments with MF1 suggesting VEGFR1 plays an important role ing pain transmission (FIG. 7).

Genetic evidence. Vegfr1tk$^{-/-}$ mice, which globally lack the Flt1 tyrosine kinase domain, are insensitive to OA knee pain, supporting the data that Flt1 activation is involved in OA pain sensitization (FIG. 8; p<0.01; *p<0.001 vs. sham; ns, not significant). Pain sensitization by Flt1 is not limited to knee OA. Similar effects were observed in the OA-like disc degeneration disease (DDD) animal model that induces low back pain (LBP). Vegfr1tk$^{-/-}$ mice showed markedly reduced LBP (FIG. 9A), despite the fact that development of pathological changes in WT and Vegfr1tk$^{-/-}$ mice are similar (FIG. 9B). The data shows a role for Flt1 in pain transmission.

Flt1 (not Flk1) plays a role in DRG sensory neuronal plasticity. It was found that increased retrograde axonal transportation of VEGF-A to innervating neuronal cell bodies is selectively via Flt1; and anti-VEGF Ab or pazopanib completely abolished activation of Flt1 (not Flk1) in DRG sensory neurons. The data show that increased VEGF in OA knee joints can be retrogradely transported to the DRG through Flt1-expressing nerve terminals, which are increased in OA joints, and play a role in sensory neuronal plasticity, directly modulating the excitability of the neurons.

The data demonstrates that increases in sensory nerve terminals in synovium predict joint pain sensitization in OA patients and have a strong correlation with increases in nerve growth-promoting factors such as VEGF and NGF that potently stimulate sensory neuronal distribution in joint synovium.

Example 2: Activation of Flt1 Drives OA-Associated Persistent Chronic Joint Pain Through Activation of Spinal Glial Cells, Showing that Pain Reduction by Targeting Flt1 is by Blockage of the Pain Transmission at the Central Level VEGF-A induces pain hypersensitivity through effects in the peripheral nervous system (PNS) and central nervous system (CNS). IA injection of Flt1 ligand (but not Flk1 ligand) caused mechanical hypersensitivity within 30 min (FIG. 2), showing that Flt1 ligands can directly activate the PNS to induce pain. Additionally, it was reported that animals with chronic OA pain had increased spinal levels of VEGF-A (FIG. 10). Consistent with reports that VEGF and Flt1 are highly expressed in reactive astrocytes in CNS (Thompson W L, et al. Brain Res. 2009 Sep. 1; 1287:47-57. Erratum in: Brain Res. 2009 Oct. 27; 1295:230; and Brambilla R, et al. JEM 2005, 202(1):145), the triple immunofluorescence (IF) staining shows that the cellular source of VEGF is, in fact, astrocytes. Importantly, intrathecal (i.t.) injection (spinal injection) of VEGF-A acutely induced mechanical hyperalgesia in a dose-dependent fashion (FIG. 11), showing a direct role of VEGF in modulating central pain perception. Given the similar dose (10 ng) and time course of mechanical hyperalgesia following IA injection (FIG. 2) and i.t. injections of VEGF-A (FIG. 11), VEGF signaling appears to be equally able to induce pain hypersensitivity in the PNS and CNS.

Indeed, the development of hypersensitivity to pain in response to VEGF injection differs from responses to nerve growth factor (NGF), a well-known OA pain mediator. IA injection of NGF acutely increased mechanical allodynia (Kc R, et al. Ann Rheum Disease 2016 75(12):2133) but, surprisingly, i.t. injection of NGF showed no pain response, suggesting that CNS levels of pain perception are involved in VEGF-induced pain, but not in NGF-induced joint pain. These results indicate that Flt1 activation can directly induce DRG sensory neuronal plasticity, which leads to sensory neuronal outgrowth stimulation and rapid enhancement of nociceptive synaptic transmission in the spinal dorsal horn (central sensitization). These pain transmission activities can facilitate sustained chronic pain during the development of OA.

IA injection with pazopanib reduces spinal activation of NFκB-glial axis that is correlated with OA joint pain. Glial cells play a role in pain sensitization in neuropathic pain. In the OA model, the development of OA pain and spinal astroglial activation were strongly correlated (FIG. 12, sham vs. 12 week post OA). IA injection of pazopanib (twice/week, 70 µg/kg) abolished this spinal astroglial activation, showing: (i) a link between chronic OA pain and spinal astroglial activation; and (ii) VEGF/VEGFR signaling-dependent astroglial activity at central levels. NF-κB is the important regulator for glial activation (Brambilla R., JEM 2005, 202(1): 145). This idea was supported using transgenic mice in which astroglial NF-κB activity was inhibited (Tg$^{GFAP-IκBα-dn}$ referred as Tg$^{dn}$), resulting in astroglial inactivation. These Tg$^{dn}$ mice showed insensitivity to OA pain.

Astroglial activation modulates microglial activation in an OA pain animal model. Astroglia and microglial both are known to be involved in pain perception. During OA progression, it was found that microglia are transiently activated mainly in early OA stage (4 week-post OA induction), but that the activation is no longer sustained in advanced OA pain (12 week) (WT). Activated microglia promote astrocytic activation (Brambilla R., et al. Brain Res. 2009; 1287:47-57). The results show that astrocyte activation subsequently stimulates microglial activation. These results show pain transmission from acute to chronic OA joint pain. Double IF staining of spinal dorsal horn was compared with and without OA (sham vs. 4 wk-, 8 wk-post OA). Microglia in Tg$^{dn}$ mice (astroglia cells are inactivated in spinal cord) showed no activation in early OA stage (4 wk-post OA induction), showing astrocyte-dependent microglial activation in the development of early OA pain.

Example 3: Nanomedicine Technology-Based Drug Formulation of Pazopanib (Nano-PAZ) Prolongs and Sustains Drug Efficacy for >16 Weeks by a Single IA Injection in the Pre-Clinical OA Animal Model Pazopanib was intraarticularly injected twice per week to observe its continuing pain reduction effect. To facilitate application of nano-PAZ at clinical setting, a nanotechnology-based formulation of pazopanib (nano-PAZ) that prolongs drug effects with sustained joint pain relief for months by a single IA injection was developed.

Nanoparticles of PEG-PCL (5k-b-6.5k) encapsulating pazopanib were prepared by the flash nanoprecipitation method using a multi-inlet vortex mixer (MIVM) (FIG. 13, nano-PAZ(I)). The resulting composition was intraarticularly injected into the knee joint of mice at the inflammatory pain stage (at one week after OA induction by surgery). Weekly behavioral pain tests revealed that 5 mL (6.5 mg/mL, total 32.5 µg/knee) of the nano-formulation was effective in reducing pain for >12 weeks (FIG. 13).

The release of the drug in nano-PAZ(I) was slow in the beginning, and took 4 weeks to achieve a full pain-relieving effect. The drug formulation was modified to increase the initial burst release of the drug, but at the same time, maintain the sustained release property and stability using nanoparticles of PLGA. PEGylated liposome formulation was added to coat the polymeric nanoparticles. These nanoparticles used for the formulation of nano-PAZ are biodegradable and biocompatible polymers that are FDA-approved for both injection and oral administration. The scalable methods developed allow to generate reproducible nano-PAZ formulations with well controlled physicochemical properties. The results show that a single IA injection of 2.5 mL (13 mg/mL, total 32.5 mg/knee) at inflammatory pain stage (IA drug administration a week after surgery) rapidly reduces joint pain in the beginning showing almost immediately full pain-relieving effect that sustains for >16 weeks in the OA model with consistency (FIG. 14, Nano-PAZ(II)).

Materials and methods of making nanoformulations of Pazopanib. Polyethylene glycol-b-polycaprolactone amphiphilic diblock copolymer (Mw 5k-6.5k) (PEG-b-PCL) (5k-b-6.5k) was purchased from Polymer Source, Inc. Pazopanib was purchased from LC Laboratories. Poly(lactic-co-glycolic acid) (PLGA, acid terminated; PLA:PGA 50:50 w/w; Mw 7000-17000), dimethyl sulfoxide (DMSO), chloroform $(CHCl_3)$ were purchased from Sigma-Aldrich (St Louis, MO), 1,2-dipalmitoyl-sn-glycero-3-phosphoethanolamine-N-[azido(polyethylene glycol)-2000 (ammonium salt) (DPPE-PEG2k) and L-α-phosphatidylcholine (Soy PC) were purchased from Avanti Polar Lipids, Inc (Alabaster, AL).

Pazopanib loaded PEG-PCL (5k-6.5k) nanoparticle preparation method (Nano-PAZ I). Nanoparticles of PEG-b-PCL(5k-b-6.5k) encapsulating pazopanib were generated by flash nanoprecipitation method using a multi-inlet vortex mixer (MIVM) (Liu, Y., et al. (2008) Chemical Engineering Science, 63(11), 2829-2842; Szymusiak, M., et al. (2016). 511(1), 415-423; and Shen, H., et al. (2011) Journal of Nanoparticle Research, 13(9), 4109-4120. One of the four inlet streams (stream 1) containing 0.025 wt % PEG-b-PCL and 0.025 wt % pazopanib dissolved in DMSO. The other three inlet streams contained deionized water as anti-solvent to precipitate the polymer and the drug. The flowrate of stream 1 and stream 2 was set to be 6 ml/min while flowrate of stream 3 and 4 was 54 ml/min. The nanoparticle suspension (200 ml) was collected into a beaker containing 250 ml solution of leucine (6 µg/ml) in deionized water under stirring, which was then dialyzed against 6 µg/ml leucine-deionized water solution using a cellulose membrane (with MWCO 3.5 kDa) for 48 hours to remove DMSO. The solution for dialysis was changed every 2 to 4 hours. After that, the nanosuspension was freeze-dried for 72 hours to produce stable solid power. Upon dosing to the animals, the nanoparticles were re-suspended in PBS buffer solution with a drug concentration 6 mg/ml.

Pazopanib loaded PLGA (7k-17k) nanoparticle preparation method (Nano-PAZ II). Liposomes (5 mM) containing 95 mol % Soy PC and 5 mol % DPPE-PEG2k was prepared using thin film dehydration method. The details are as follows: 147.3 uL of Soy PC (25 mg/ml in chloroform) and 27.5 uL of DPPE-PEG2k (25 mg/ml in chloroform) were pipetted in a scintillation vial and dried under a gentle stream of Argon gas. The dried film was then placed under vacuum for an additional 2 hours to remove any residual traces of organic solvent. The desiccated film was subsequently rehydrated with 1 mL of filtered, deionized water (DI $H_2O$) and bath-sonicated for approximately 3 minutes. The solution was then extruded 21 times with 200 nm polycarbonate membrane and stored at 4° C. for later use.

Nanoparticles of PLGA (7k-17k) encapsulating pazopanib were generated by flash nanoprecipitation method similarly to the description in the previous section of producing PEG-b-PCL nanoparticle encapsulating pazopanib. One of the four inlet streams of MIVM (stream 1) containing 0.025 wt % PLGA and 0.025 wt % pazopanib dissolved in DMSO. The other three inlet streams contained deionized water as anti-solvent to precipitate the polymer and the drug. The flowrate of stream 1 and stream 2 was set to be 6 ml/min while flowrate of stream 3 and 4 was 54 ml/min. The nanoparticle suspension (88 ml) was collected into a beaker containing 120 ml solution of leucine (6 µg/ml) and 0.2 mL of liposome (5 mM) solution in deionized water under stirring. The mixture was then bath-sonicated for 6 min for the liposomes to wrap around polymeric nanoparticles. The solution was dialyzed against the solution of 6 µg/ml leucine in deionized water using a cellulose membrane (with MWCO 3.5 kDa) for 48 hours to remove DMSO. The solution for dialysis was changed every 2 to 4 hours. After that, the nanosuspension was freeze-dried for 72 hours to produce stable solid power.

Nanoparticle characterization. Drug loading was 22% by mass for Paz-PEG-PCL and Paz-PLGA nanoparticle. Drug encapsulation rate was 86.4% for Paz-PEG-PCL and 89.6% for Paz-PLGA.

To measure drug loading (DL) and drug encapsulation efficiency (EF) of pazopanib in polymeric nanoparticles, the suspension was first dialyzed and then freeze-dried. During the dialysis process, unencapsulated pazopanib and DMSO were removed. The dried powder was re-dissolved in DMSO at the solid construct of 1 mg/ml. The amount of pazopanib was quantified using High Performance Liquid Chromatography (HPLC) at the absorbance wavelength of 270 nm.

$$DL\,(\%) = \frac{\text{Amount of pazopanib encapsulated in nanoparticles}}{\text{Total weight of nanoparticles}} \times 100\%$$

$$EF(\%) = \frac{\text{Amount of pazopanib encapsulated in nanoparticles}}{\text{Feeding weight of pazopanib}} \times 100\%$$

Nanoparticle size distributions after flash nanoprecipitation and re-suspension were measured by using dynamic light scattering (DLS) (Malvern, Cambridge, UK). The average hydrodynamic diameter of the nanoparticles right after flash nanoprecipitation and after re-suspension were 550 nm and 600 nm, respectively (FIG. 15 and FIG. 16).

Measurements of pazopanib in vitro release. The dried powder was resuspended at 0.5 mg/ml of pazopanib concentration to monitor the drug release in acetate buffer at pH 3. The custom-made setup consists of two glass chambers separated by the cellulose membrane (with MWCO 3.5 kDa). The bottom chamber contained the nanoparticle suspension and the top chamber contained ammonium acetate buffer (pH 3). The setup was left in 37° C. oven and the sample was collected from the top chamber and replaced with fresh buffer. The stir bars were added to prevent sedimentation of the particles at the bottom of the chambers. The amount of pazopanib in the collected sample was quantified using HPLC and drug release was calculated (FIG. 17). Samples are set up in a 37° C. oven and the release was taken over a 120-day period. Concentration of Pazopanib inside the nanoparticles for both formulations was 0.5 mg/ml. The amount of Pazopanib release was determined using HPLC.

Example 4: Nanomedicine Technology-Based Drug Formulation of Pazopanib (Nano-PAZ) Markedly Prolongs Joint Pain Relief for >16 Weeks and Protects Cartilage from Degeneration by a Single IA Injection in the Pre-Clinical OA Animal Model Described herein are improved drug formulations, nano-PAZII and nano-PAZIII, that in the presence and/or absence of mesenchymal stem cells for OA and other musculoskeletal pain treatment and can alleviate pain-associated depression.

Pazopanib has been intraarticularly injected twice per week to observe the continuing pain reduction effect. To facilitate application of nano-PAZ at a clinical setting, a nanotechnology-based formulation of pazopanib (nano-PAZ) that prolongs drug effects with sustained joint pain relief for months by a single IA injection was developed.

Generation of nano-PAZII. Pazopanib encapsulated in nanoparticles of PEG-PCL (5k-b-6.5k). Pazopanib was encapsulated in nanoparticles of PEG-PCL using flash nano-precipitation and a multi-inlet vortex mixer (MIVM) custom-made. The resulting nanomedicine (nano-PAZII) was intraarticularly injected into the knee joints of preclinical OA mice (a single IA injection) at the time of joint injury (inflammatory pain stage). Weekly behavioral pain tests revealed that a single injection of 32.5 mg/knee of nano-PAZII markedly reduces joint pain for >16 weeks and shows almost a full protection of cartilage from degeneration (FIG. 18).

Partial cartilage protection by a single IA nano-PAZII treatment was obtained when the treatment started at the later stage of OA. Almost full-cartilage protection was achieved when treatment was started at the time of joint injury (FIG. 18). Excellent and rapid pain relief and cartilage protection was observed when the treatment began at the early OA stage (FIG. 19). significant pain relief was still observed with partial cartilage protection when treatment was started at the advanced OA stage (FIG. 20).

A single IA co-treatment of nano-PAZII with mesenchymal stem cells (MSCs) at early OA stage markedly improved cartilage preservation, suggesting an enhanced tissue regenerative impact by the combination of nano-PAZII and MSCs. Although nano-PAZ offers superior pain reduction and inhibition of cartilage degeneration compared to clinically approved other treatment options (IA injection of HA, PRP, or steroids) (Kroin et al. Gene. 2016, 10: 591(1):1-5), the best results were seen when treatments were started in earlier time points (e.g., at the time of injury) in the preclinical OA animal model. If treatments begin at later stages of OA, the outcomes showing preservation of cartilage (associated with joint function) are less compared to treatment regimens that began at the time of joint injury or earlier during OA progression. OA patients often seek medical help when the disease is near an advanced stage of disease progression (with worn-out cartilage tissue and excruciating joint pain). Preserving cartilage in advanced OA stages is challenging due to the lack of cellularity (worn-out cartilage) and the limited repair capacity of chondrocytes.

To evaluate the efficacy of combined treatments with bone-marrow-derived MSCs (cell-based therapy, purchased from Cyagen) and nano-PAZII for improved cartilage tissue regeneration, post-trauma-induced OA (PMM) was generated in mice, treated with a single IA injection (using 30 G needle) of nano-PAZII (32.5 mg/joint) and naive MSCs ($6\times10^4$ cells in 10 µl saline) treatment starting around 4-5 weeks post-PMM. Cell dose is based on previous studies using bone-marrow-derived MSCs in mouse OA models (Sun et al. J. Transl. Med. 16, 1-12 (2018). Joint tissues were harvested from the animals at 16 weeks post-PMM for histopathological analyses.

Improved joint pain relief by the combined therapy of nano-PAZII and MSCs (FIG. 21). A single IA injection of nano-PAZII combined with MSCs significantly improves cartilage regeneration (diamonds) compared to nano-PAZII alone (triangles) (FIG. 21, **p<0.01 between nano-PAZII alone and nano-PAZII with naïve MSCs).

Markedly improved cartilage protection/regeneration by the combined therapy of nano-PAZII and MSCs (FIG. 22). A single IA injection of nano-PAZII combined with naive MSCs significantly improves cartilage regeneration compared to nano-PAZII alone (FIG. 21, **p<0.01 between nano-PAZII alone and nano-PAZII with naïve MSCs).

A single IA injection of naive MSCs cannot survive long in the joint microenvironments. It has been reported that IA-injected MSCs remained in the synovial cavity and were detectable up to 1-month post-injection with a significantly reduced number of cells (Satue et al. Scientific Rep. 2019, 9:10153). Improving cell viability after IA injection can generate efficient MSC based OA therapies. Inhibition of VEGF signaling pathways by a soluble VEGFR protein markedly increased the stability of MSCs, promoting the cartilaginous phenotype in OA treatment. Taken together, combined treatment of nano-PAZ and MSCs can be used for the treatment of any stage of OA disease progression.

Example 5: Generation of Nano-PAZIII

Comparing the rapid and effective pain reduction by IA pazopanib treatments (see FIG. 4), the pain reduction by nano-PAZII is not efficient, taking more than 4 weeks to be close to the pain-free level (see FIG. 18). The drug formulation was further modified to increase the initial burst release of the drug, but at the same time, maintain the sustained release property and stability using nanoparticles of PLGA (nano-PAZIII). PEGylated liposome formulation was added to coat the polymeric nanoparticles. These nanoparticles used for the formulation of nano-PAZ are biodegradable and biocompatible polymers that are FDA-approved for both injection and oral administration. The scalable methods developed allow to generate reproducible a nano-PAZIII formulation with well controlled physico-chemical properties. The results show that a single IA injection of nano-PAZIII (total 65 µg/knee) at inflammatory pain stage (IA drug administration a week after surgery) rapidly reduces joint pain in the beginning showing almost immediately full pain relieving effect within a week after injection that sustains for >16 weeks in the OA model with consistency (FIG. 23A, nano-PAZII vs. nano-PAZIII).

A single IA injection of nano-PAZIII showed rapid and effective pain reduction at the disease treatment time points measured: (i) at the time of joint injury (treatment begins at the inflammatory pain stage), (ii) treatment starts at early OA stage (4-5 weeks post-OA) and (iii) treatment starts at advance OA stage (8-9 weeks post-OA) during the course of OA disease progression (see FIG. 24).

Pain reduction by nano-PAZIII is significantly faster than nano-PAZII. However, both drugs show a similar cartilage protection power by a single IA treatment. A single IA injection was done with either nano-PAZII (FIG. 25) or nano-PAZIII (FIG. 26) at the time of knee OA induction by PMM surgery (inflammatory pain stage). After 16 weeks post-PMM, animals were sacrificed, joint tissues were harvested for biochemical and histopathological analyses with OARSI score for quantitation of joint pathology.

A single IA injection of nano-PAZIII reduces knee joint pain as well as OA associated depression. More recently, serious concerns have been raised regarding OA-related chronic comorbid health conditions. For example, individuals with OA have a 2.5-times greater risk of having three or more other chronic conditions. Compared to civilians, veterans are far more vulnerable to a chronic comorbid health condition (Richardson L M, et al., SAGE Open Medicine, 2016. 4:1-11; and Clark-Raymond A, and Halaris A. J Psychiatric Research, 2013 47:1080) with more than a third of veterans suffering from at least two such chronic conditions (e.g., OA and depression) (Nowacka-Chmielewska M M, et al., Experimental and Therapeutic Medicine 2017, 13:723; and Zheng S, et al., BMC Musculoskeletal Disorders 2021 22:40). In particular, OA patients show a higher prevalence of the devastating symptoms of depression and anxiety than those without OA. Arthritic conditions and depression comorbidity magnify the persistent joint pain sensitization, which, in turn, worsens the depression. As OA is the most prevalent form of arthritis, depression is the most prevalent psychiatric disorder, ranking in the top five leading causes of disability worldwide (Roughan W H, et al., Frontiers in Psychiatry, 2021, 12:1; and McClendon J, et al., Arthritis Care & Research 2021 73:11). Every day, 17.6 U.S. veterans commit suicide, primarily due to the ramifications of untreated depression (2020 National Veteran Suicide Prevention Annual Report. Office of Mental Health and Suicide Prevention. VA). These reports indicate an urgent unmet need to improve treatment strategies to manage OA symptoms and prevent depression, a comorbid chronic disease in OA patients (Roughan W H, et al., Frontiers in Psychiatry 2021, 12:1).

The comorbid joint pain and depression make clinical management extraordinarily challenging and complicated. For example, patients with comorbid OA pain and depression showed significantly reduced benefits from taking anti-depressant drugs compared to those without joint pain (Kroin J S, et al. Gene. 2016 10; 591(1):1-5). The mechanisms that drive this reduction are unknown. Thus, there is a second urgent unmet need to understand the underlying mechanisms to address depressive symptoms, manage OA disease better, and develop an effective treatment strategy for OA-associated comorbid conditions. OA-associated depression has often resulted from chronic joint pain affecting mobility and physical limitations, which in turn stirs feelings of depression. Researchers have pointed out that OA-induced social impairment (e.g., social isolation, difficulty walking around the block and talking to neighbors, shopping with friends, cooking dinner for friends, and social stresses (Vasquez and Peterson. J Pharmacol Exp Ther 2017, 361:87-98), etc.) is linked to increased depression among individuals with OA. Importantly, patients with comorbid OA pain and depression show minimal or no benefit from taking anti-depressant drugs compared to patients without joint pain. The results described herein found that increased depression levels among the animals with knee joint OA are significantly reduced by the single IA treatment with nano-PAZIII (FIG. 27, **p<0.01).

The additional significance of targeting VEGFR1/Flt1 and VEGFR2/Flk1 by nano-PAZ. The compositions comprising nano-PAZ and the methods thereof can be used to treat subjects with knee OA as well as other musculoskeletal joint disorders and pain, including but not limited to treatment of lower back pain and to protect disc tissue; another serious chronic disease that commonly occurs in veterans and civilians.

We claim:

1. A nanoparticle comprising or consisting of Pazopanib encapsulated by poly (lactic-co-glycolic acid) (PLGA), poly (ethylene glycol)-b-poly (e-caprolactone) (PEG-b-PCL), or a combination thereof, wherein the nanoparticle is in a pegylated liposome.

2. The nanoparticle of claim 1, wherein the nanoparticle has a diameter of from 500 nm to 600 nm.

3. The nanoparticle of claim 1, wherein the nanoparticle comprises about 2 to about 25 weight percent of the Pazopanib.

4. The nanoparticle of claim 1, wherein the ratio of PLGA to Pazopanib is approximately 1:1.

5. The nanoparticle of claim 1, further comprising a cryo-protective agent.

6. The nanoparticle of claim 1, wherein the nanoparticle further contains a positively charged molecule or a positively charged lipid.

7. A pharmaceutical composition comprising one or more of the nanoparticles of claim 1.

8. The pharmaceutical composition of claim 7, wherein the encapsulation efficiency of Pazopanib is between 80% and about 90%.

9. The pharmaceutical composition of claim 7, wherein the pharmaceutical composition is formulated as a liquid, a lyophilized powder, a cream, or an ointment.

10. The pharmaceutical composition of claim 7, wherein the pharmaceutical composition is substantially free of dimethylsulfoxide (DMSO), methanol, and/or chloroform.

11. A method of inhibiting cartilage degeneration in a subject, the method comprising administering to a subject in need thereof a therapeutically effective amount of a composition comprising the nanoparticle of claim 1.

12. A method of reducing pain or reducing joint pain in a subject, the method comprising administering to a subject in need thereof a therapeutically effective amount of a composition comprising the nanoparticle of claim 1.

13. A method of treating osteoarthritis in a subject in need thereof, the method comprising administering to a subject in need thereof a therapeutically effective amount of a composition comprising the nanoparticle of claim 1.

14. A method of treating a joint condition in a subject in need thereof, the method comprising administering to a subject in need thereof a therapeutically effective amount of a composition comprising the nanoparticle of claim 1.

15. The method of claim 14, wherein the joint condition is a joint injury.

16. The method of claim 15, wherein the joint injury is a traumatic injury or a post-operative injury.

17. The method of claim 15, wherein the joint injury is a repetitive strain injury.

18. A method of enhancing tissue regeneration in a subject in need thereof, the method comprising administering to a subject in need thereof a therapeutically effective amount of a composition comprising the nanoparticle of claim 1 and mesenchymal stem cells.

19. The method of claim 18, wherein the administration is via intraarticular administration.

\* \* \* \* \*